(12) United States Patent
Muir et al.

(10) Patent No.: US 10,131,950 B2
(45) Date of Patent: Nov. 20, 2018

(54) METHOD TO PREDICT HERITABLE CANINE NON-CONTACT CRUCIATE LIGAMENT RUPTURE

(71) Applicant: Wisconsin Alumni Research Foundation, Madison, WI (US)

(72) Inventors: Peter Muir, Madison, WI (US); Lauren Baker, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 80 days.

(21) Appl. No.: 15/010,491

(22) Filed: Jan. 29, 2016

(65) Prior Publication Data

US 2016/0222451 A1   Aug. 4, 2016

Related U.S. Application Data

(60) Provisional application No. 62/109,336, filed on Jan. 29, 2015.

(51) Int. Cl.
| | |
|---|---|
| *C12Q 1/68* | (2018.01) |
| *C07H 21/04* | (2006.01) |
| *C12Q 1/6883* | (2018.01) |
| *A01K 67/02* | (2006.01) |

(52) U.S. Cl.
CPC ............ *C12Q 1/6883* (2013.01); *A01K 67/02* (2013.01); *C12Q 2600/118* (2013.01); *C12Q 2600/124* (2013.01); *C12Q 2600/156* (2013.01); *C12Q 2600/16* (2013.01); *C12Q 2600/172* (2013.01)

(58) Field of Classification Search
None
See application file for complete search history.

(56) References Cited

U.S. PATENT DOCUMENTS 7,510,841 B2   3/2009   Stuelpnagel et al.

OTHER PUBLICATIONS

Baird et al. (Stichting International Foundation for Animal Genetics, vol. 45, pp. 542-549, (Year: 2014).*
Illumina (Canine HD Bead Chip, 170K Chip, DataSheet: DNA Genotyping, 2010). (Year: 2010).*
Baird et al. (Connect Tissue Res, Early Online Apr. 1-7, 2014) (Year: 2014).*
Clements et al. (The Am. Genetic Association, vol. 101, No. 1, pp. 54-60, 2010) (Year: 2010).*
Safra et al. (Veterinary Journal, vol. 189, pp. 220-226, 2011) (Year: 2011).*
Tiira et al. (PLoS ONE, vol. 7, No. 7, e41684, Jul. 2012) (Year: 2012).*
Tacher et al. (J. of Heredity, vol. 96, No. 7, pp. 812-816, 2005) (Year: 2005).*
DPPA3 Gene Cards, Human Gene Database (Year: 2017).*
Alentorn-Geli et al. (2009). Prevention of non-contact anterioro curicate ligament injuries in soccer players. Part 1: Mechanisms of injury and underlying risk factors. *Knee Surgery, Sports, Traumatology, Arthroscopy.* 17:705-729.
Baird et al. (2014). Genome-wide association study identifies genomic regions of association for cruciate ligament rupture in Newfoundland dogs. *Animal Genetics.* 45, 4: 542-549.
Beynnon et al. (2006) The relationship between menstrual cycle phase and anterior cruciate ligament injury. *Am J Sports Med.*, 34: 757-764.
Bleedorn et al. (2011). Synovitis in dogs with stable stifle joints and incipient cranial cruciate ligament rupture: A cross-sectional study. *Veterinary Surgery.* 40: 531-543.
Chang et al. (2015) Second-generation PLINK: rising to the challenge of larger and richer datasets. *GigaScience.* 4:7.
Chen et al. (2011) A genetic risk score combining ten psoriasis risk loci improves disease prediction. *PLoS One.* 6: e19454.
Chuang et al. (2014), Radiographic risk factors for contralateral rupture in dogs with unilateral cranial cruciate ligament rupture in dogs with unilateral cranial cruciate ligament rupture, PLOS ONE, 9:9:e106389, 1-10.
Clements et al. (2011). Risk of canine cranial cruciate ligament rupture is not associated with the major histocompatibility complex. *Veterinary and Comparative Orthopaedics and Traumatology.* 1-3.
Flynn et al. (2005). The familial predisposition toward tearing the anterior cruciate ligament. *The American Journal of Sports Medicine.* 33: 23-28.
Ghosh et al. (2008) Estimating odds ratios in genome scans: An approximate conditional likelihood approach. *Am J Human Genet.* 82: 1064-1074.
Girling et al. (2006). Use of biochemical markers of osteoarthritis to investigate the potential disease-modifying effect of tibial plateau levelling osteotomy. *Journal of Small Animal Practice.* 47: 708-714.
Hayashi et al. (2004). Cranial cruciate ligament pathophysiology in dogs with cruciate disease: A review. *Journal of the American Animal Hospital Association.* 40: 385-390.
Hewett et al. (2007) Effects of the menstrual cycle on anterior cruciate ligament injury risk. *Am J Sports Med.* 35: 659-668. [33,34].
Hoffman et al. (2013) A unified framework for penalized multiple regression analysis of GWAS data. PLoS Comput Biol. 9: e1003101.
Huang et al. (2009) Systematic and integrative analysis of large gene lists using DAVID bioinformatics resources. *Nat Protoc.* 4: 44-57.
Huang Q. (2015) Genetic study of complex diseases in the post-GWAS era. *J Genet Genomics.* 42: 87-98.
Karlsson et al. (2008). Leader of the pack: gene mapping in dogs and other model organisms. *Nature Reviews Genetics.* 9: 713-725.
Karlsson et al. (2013) Genome-wide analyses implicate 33 loci in heritable dog osteosarcoma, including regulatory variants near CDKN2A/B. *Genome Biol.* 14: R132.

(Continued)

*Primary Examiner* — Jeanine A Goldberg
(74) *Attorney, Agent, or Firm* — Joseph T. Leone, Esq.; Dewitt Ross & Stevens S.C.

(57) ABSTRACT

Method and kits for diagnosing propensity to non-contact cranial cruciate ligament rupture (CCLR) in a dog are described. The method includes isolating genomic DNA from a dog and then analyzing the genomic DNA from step for a single nucleotide polymorphism occurring in selected loci that have been determined to be associated with the CCLR phenotype via a genome-wide association study.

20 Claims, 8 Drawing Sheets

Specification includes a Sequence Listing.

(56) References Cited

OTHER PUBLICATIONS

Kendrew et al. (eds.), "The Encyclopedia of Molecular Biology," published by Blackwell Science Ltd., 1994 (ISBN 0-632-02182-9) (Book—Copy Not Provided).
Khoschnau et al. (2008). Type I collagen alphal sp 1 polymorphism and the risk of cruciate ligament ruptures or shoulder dislocations. *The American Journal of Sports Medicine*. 36: 2432-2436.
Kim et al. (2011) Radiographic quantitative assessment of cranial tibial subluxation before and after tibial plateau leveling osteotomy in dogs. *Am J Vet Res*. 72: 420-416.
Lee et al. (2012) INRICH: interval-based enrichment analysis for genome-wide association studies. Bioinformatics. 28: 1797-1799.
Benjamin Lewin, "Genes V," published by Oxford University Press, 1994 (ISBN 0-19-854287-9) (Book—Table of Contents Provided Only).
Lindblad-Toh et al. (2005) Genome sequence, comparative analysis, and haplotype structure of the domestic dog. *Nature*. 438: 803-819.
Mannion et al. (2014) Genes encoding proteoglycans are associated with risk of anterior cruciate ligament ruptures. *Br J Sports Med*. 48: 1640-1646.
Muir P. (1997) Physical examination of lame dogs. *Comp Cont Ed Pract. Vet* 19: 1149-1161.
Muir et al. (2011) Contralateral cruciate survival in dogs with unilateral non-contact cranial cruciate ligament rupture. *PLoS ONE*. 6(10): e25331.
Nielen et al. (2001) Heritability estimations for diseases, coat color, body weight, and height in a birth cohort of Boxers. *Am J Vet Res*. 62: 1198-1206.
Obeidat et al. (2014) TIMAP promotes angiogenesis by suppressing PTEN-mediated Akt inhibition in human glomerular endothelial cells. *Am J Physiol Renal Physiol*. 307: F623-F633.
Ostrander et al. (2005). The canine genome. *Genome Research*. 15: 1706-1716.
Park et al. (2010) Estimation of effect size distribution from genome-wide association studies and implications for future discoveries. *Nat Genet*. 42: 570-575.
Pérez et al. (2014) Genome-wide regression and prediction with the BGLR statistical package. *Genetics*. 198: 483-495.
Plaas et al. (2011) Biochemical identification and immunolocalization of aggrecan, ADAMTS5 and inter-alpha-tryspin-inhibitor in equine degenerative suspensory ligament desmitis. *J Orthop Res*. 29: 900-906.
Posthumus et al. (2009) Genetic risk factors for anterior cruciate ligament ruptures: COL1A1 gene variant. *British Journal of Sports Medicine*. 43: 352-356.
Rahim et al. (2014) The association of genes involved in the angiogenesis-associated signaling pathway with risk of anterior cruciate ligament rupture. *J Orthop Res*. 32: 1612-1618.
Reif et al. (2003) Comparison of tibial plateau angles in normal and cranial cruciate deficient stifles of Labrador retrievers. *Vet Surg*. 32: 385-389.
Schierding et al. (2014) The missing story behind genome wide association studies: single nucleotide polymorphisms in gene deserts have a story to tell. *Front Genet*. 5: 39.
Schumann R. (2011) Old and new findings on lipopolysaccharide-binding protein: a soluble pattern-recognition molecule. *Biochem Soc Trans*. 39: 989-993.
Sutton et al. (2013) Anterior cruciate ligament rupture: Differences between males and females. *J Am Acad Orthop Surg*. 21: 41-50.
Svishcheva et al. (2012) "Rapid variance components-based method for whole-genome association analysis," *Nature Genetics* 44:1166-1170.
Tang et al. (2014) Candidate genes and functional noncoding variants identified in a canine model of obsessive-compulsive disorder. *Genome Biol*. 15: R25.
Waggett et al (2006) Connexin 32 and 43 gap junctions differentially modulate tenocyte response to cyclic mechanical load. *Eur J Cell Biol*. 85: 1145-1154.
Whitehair et al (1993). Epidemiology of cranial cruciate ligament rupture in dogs. *Journal of the American Veterinary Medical Association*. 203: 1016-1019.
Wilke et al (2005). Estimate of the annual economic impact of treatment of cranial cruciate ligament in jury in dogs in the United States. *Journal of the American Veterinary Medical Association*. 227(10): 1604-7.
Wilke et al (2008) Inheritance of rupture of cranial cruciate ligament in Newfoundlands. *J Am Vet Med Assoc*. 228: 61-64.
Wilke et al. (2009). Identification of chromosomal regions associated with cranial cruciate ligament rupture in a population of Newfoundlands. *American Journal of Veterinary Research*. vol. 70,8: 1013-1017.
Witsberger et al. (2008). Prevalence of and risk factors for hip dysplasia and cranial cruciate ligament deficiency in dogs. *Journal of the American Veterinary Medical Association*. 232 (12): 1818-1824.
Yang et al. (2011) GCTA: a tool for Genome-wide Complex Trait Analysis. *Am J Hum Genet*. 76-82. [PubMed ID: 21167468].
Young et al. (2009) Maturational alterations in gap junction expression and associated collagen synthesis in response to tendon function. *Matrix Biol* 2009;28: 311-323.
Zhang Ch. (2010)Nearly unbiased variable selection under minimax concave penalty. *Ann Stat*. 38: 894-942.
Zhou et al. (2013) Polygenic modeling with Bayesian sparse linear mixed models. PLoS Genetics. 9: e1003264.
Zhou et al (2012) Genome-wide efficient mixed-model analysis for association studies. *Nat Genet*. 44: 821-824.

\* cited by examiner

SEQUENCE LISTING

<160> NUMBER OF SEQ ID NOS: 1

<210> SEQ ID NO 1

```
<211> LENGTH: 4
<212> TYPE: PRT
<213> ORGANISM: Canis familiaris

<400> SEQUENCE: 1

Asp Glu Ala His
1
```

METHOD TO PREDICT HERITABLE CANINE NON-CONTACT CRUCIATE LIGAMENT RUPTURE

CROSS-REFERENCE TO RELATED APPLICATIONS

Priority is hereby claimed to provisional application Ser. No. 62/109,336, filed Jan. 29, 2015, which is incorporated herein by reference.

BACKGROUND

The domestication of the dog and subsequent development of many dog breeds has been declared one of the greatest genetic experiments ever conducted by human beings. [Ostrander, E. A., Wayne, R. K. (2005).] The canine genome. *Genome Research.* 15: 17061716. There are now over 300 unique breeds of dog. These breeds have been purposefully developed with specific behavioral and physical traits in mind, thereby showcasing the incredible genetic diversity of the species—from Great Danes to Chihuahuas. However, an unintended consequence of breed development is an increased incidence of disease states within certain breed. Many of the same disease states seen in certain dog breeds are also seen in human beings. Notably, the reduced genetic diversity in purebred dogs has generated stretches of linkage disequilibrium (LD) that are 40 to 100 times longer in dogs than in humans. [Karlsson, E. K., Lindblad-Toh, K. (2008). Leader of the pack: gene mapping in dogs and other model organisms. *Nature Reviews Genetics.* 9: 713-725.] This presents a unique opportunity to study the genetic predisposition to disease more efficiently by first identifying associations in dogs and using that knowledge to inform human medical research.

Cruciate ligament rupture is one condition that occurs frequently in both dogs and humans. The cranial cruciate ligament (CCL) is one of two intra-articular ligaments in the canine stifle (knee) joint, the other being the caudal cruciate ligament. The CCL is analogous to the human anterior cruciate ligament (ACL), both anatomically and functionally. Both canine populations and human populations experience a condition where the CCL/ACL ruptures without a traumatic force. This is known as non-contact cruciate ligament rupture. See Alentorn-Geli, E., Myer, G. D., Silvers, H. J., Samitier, G., Romero, D., Lazaro-Haro, C., Cugat, R. (2009). Prevention of non-contact anterioro curicate ligament injuries in soccer players. Part 1: Mechanisms of injury and underlying risk factors. Knee Surgery, Sports, Traumatology, Arthroscopy. 17:705-729. Canine non-contact cranial cruciate ligament rupture (CCLR) is the most common cause of pelvic limb lameness in dogs. CCLR is diagnosed in approximately 20% of canine cases seen for lameness at university institutions. [Wilke, V. L., Robinson, D. A., Evans, R. B., Rothschild, M. F., Conzemius, M. G. (2005). Estimate of the annual economic impact of treatment of cranial cruciate ligament in jury in dogs in the United States. *Journal of the American Veterinary Medical Association.* 227(10): 1604-7.] The canine condition is characterized by progressive stifle joint synovitis and osteoarthritis that leads to gradual fraying and eventual mid-substance rupture of the cranial cruciate ligament. Instability of the stifle joint as a result of CCLR is often debilitating and requires surgical treatment. The cost of surgery and pain management has a large economic impact. It has been estimated that American pet owners alone spend more than $1 billion per year on CCLR management [Wilkie et al., supra]. When a dog presents with one stable and one unstable stifle, evidence of disease can often be found in the stable joint. [Bleedorn, J. A., Greuel, E. N., Manley, P. A, Schaefer, S. L., Markel, M. D., Holzman, G., Muir, P. (2011). Synovitis in dogs with stable stifle joints and incipient cranial cruciate ligament rupture: A cross-sectional study. *Veterinary Surgery.* 40: 531-543.] More than 50% of dogs with unilateral CCLR will ultimately go on to rupture the contra-lateral ligament. [Muir, P., Schwartz, Z., Malek, S., Kreines, A., Cabrera, S. Y., Buote, N. J., Bleedorn, J. A., Schaefer, S. L., Holzman, G., Hao, Z. (2011) Contralateral cruciate survival in dogs with unilateral non-contact cranial cruciate ligament rupture. PLoS ONE. 6(10): e25331.] While surgical stabilization does lead to clinical improvement, it does not cure the underlying mechanism that led to ligament degeneration. Thus even with surgical intervention osteoarthritis will continue to develop in the joint over time. [Girling, S. L., Bell, S. C., Whitelock, R. G., Rayward, R. M., Thomson, D. G., Carter, S. C., Vaughan-Thomas, A., Innes, J. F. (2006). Use of biochemical markers of osteoarthritis to investigate the potential disease-modifying effect of tibial plateau levelling osteotomy. *Journal of Small Animal Practice.* 47: 708-714.]

While several hypotheses have been investigated, the mechanism underlying the cruciate rupture condition in dogs and humans remains unclear. Risk factors for disease initiation and disease progression in dogs have been investigated. Neutering, weight, and gender have all been investigated as risk factors for disease initiation. However, the most important risk factor for disease initiation in dogs is breed. The prevalence of CCLR in the Newfoundland, Labrador Retriever, and Boxer has been estimated at 8.9%, 5.79%, and 5.24% respectively. In contrast, other breeds, such as the Greyhound and Old English Sheepdog, experience much lower prevalence of CCLR (0.5% and 0.97%, respectively). The Labrador Retriever breed has greater stifle joint laxity and a weaker CCL as compared to the Greyhound. Family-based pedigree studies indicate that heritability of CCLR is high for a complex trait. Data reveal a heritability estimate of 0.27 in the Newfoundland and 0.28 in the Boxer. Human medical research has also begun to look into genetics as a potential risk factor for ACL rupture. Individuals with a blood relative who has ruptured their ACL are at two-times (2×) greater risk of rupturing their own. Recent research in humans suggests that a rare COL1A1 gene variant may be protective against ACL rupture in young athletes. See Clements, D. N., Kennedy, L. J., Short, A. D. Barnes, A., Ferguson, J., Ollier, W. E. R. (2011). Risk of canine cranial curicate ligament rupture is not associated with the major histocompatibitilty complex. Veterinary and Comparative Orthopaedics and Traumatology. 1-3; Hayashi, Kei., Manley, P. A., Muir, P. (2004). Cranial cruciate ligament pathophysiology in dogs with cruciate disease: A review. Journal of the American Animal Hospital Association. 40: 385-390; Witsberger, T., Villamil, J., Schultz, L., Hahn, A., Cook, J. (2008). Prevalence of and risk factors for hip dysplasia and cranial cruciate ligament deficiency in dogs. Journal of the American Veterinary Medicial Association. 232 (12): 1818-1824; Whitehair, J. G., Vasseur, P. B., Willits, N. H. (1993). Epidemiology of cranial cruciate ligament rupture in dogs. Jornal of the American Veterinary Medical Association. 203: 1016-1019; Wilke, V. L., Conzemius, M. G., Kinghorn, B. P., Macrossan, P. E., Cai, W., Rothschild, M. F. (2006). Inheritance of rupture of cranial cruciate ligament in Newfoundlands. Journal of the American Veterinary Medical Association. 228: 61-64; Nielen, A. L., Janss, L. L., Knol, B. W. (2001). Heritability estimations for diseases, coat color, body weight, and heigh in a birth cohort of Boxers. American Journal of Veterinary Research. 62,8: 1198-1206; Flynn, R. K., Pedersen, C. L., Birmingham, T. B., Kirkley, A., Jackowski, D., Fowler, P. J. (2005). The familial predisposition toward tearing the anterior cruciate ligament. The American Journal of Sports Medicine.33: 23-28; Posthumus, M., September, A. V., Keegan, M., O'Cuinneagain, D. , Van der Merwe, W., Schwellnus, M. P., Collins, M. (2009) Genetic risk factors for anterior cruciate ligament ruptures: COL1A1 gene variant. British Journal of Sports Medicine. 43: 352-356; and Khoschnau, S., Melhus, H., Jacobson, A., Rahme, H., Bengtsson, H., Ribom, E., Grundberg, E., Mallmin, H., Michaelsson, K. (2008). Type I collagen alpha1 sp1 polymorphism and the risk of cruciate ligament ruptures or shoulder dislocations. The American Journal of Sports Medicine. 36: 2432-2436.

Two studies have mapped the CCLR trait to the canine genome. Associations with CCLR were reported on canine chromosomes 3, 5, and 15 using a broad genomic scan of 495 microsatellite markers in Newfoundland dogs. [Wilke, V. L., Zhang, S., Evans, R. B., Conzemius, M. G., Rothschild, M. F. (2009). Identification of chromosomal regions associated with cranial cruciate ligament rupture in a population of Newfoundlands. *American Journal of Veterinary Research*. Vol. 70,8: 1013-1017.] More recently, a high-resolution genome-wide association study (GWAS) for CCLR, also in the Newfoundland breed, found single nucleotide polymorphism (SNP) associations on canine chromosomes 1, 3, 10, 12, 22, and 33. [Baird, A. E. G., Carter, S. D., Innes, J. F., Ollier, W., Short, A. (2014). Genome-wide association study identifies genomic regions of association for cruciate ligament rupture in Newfoundland dogs. Animal Genetics. 45, 4: 542-549.] The 65 most significant SNPs were re-genotyped with a custom chip array, which identified significant regions on chromosomes 1, 3, and 33. These regions contained several genes that are highly expressed in the nervous system, suggesting a potential neuronal signaling component to CCLR risk. The Baird et al. GWAS was unable to replicate results from the earlier Wilkie et al. microsatellite marker study.

SUMMARY OF THE INVENTION

To advance understanding of the genetic risk factors contributing to CCLR, a GWAS was performed to identify candidate genomic regions associated with the CCLR trait. To take advantage of the long-range LD present in dogs, the GWAS was limited to a single high-risk breed, the Labrador retriever, which has a high prevalence of CCLR. The Labrador retriever is also the most common breed in the United States according to records of the American Kennel Club.

As disclosed herein, CCLR is associated with multiple regions of the canine genome. Thus, by analyzing dogs for mutations in these CCLR-associated regions, the propensity of their progeny to carry the trait, and thus to experience CCLR, can be determined. This information can then be used to guide breeding efforts to reduce the occurrence of CCLR.

Thus, disclosed herein is a method for diagnosing propensity to non-contact cranial cruciate ligament rupture (CCLR) in a dog. The method comprises isolating genomic DNA from a dog and then analyzing the genomic DNA for single nucleotide polymorphisms occurring within, or in a genomic interval of about 2 Mb upstream or downstream of, at least one locus revealed herein to be associated with the CCLR phenotype. These loci include BICF2P1126668, BICF2P260555, BICF2P599385, BICF2P1465216, BICF2S23135243, BICF2P170661, TIGRP2P78405, BICF2P890246, BICF2P401973, BICF2G630114782, BICF2G630815470, BICF2G630815474, BICF2S23448539, BICF2P1121006, BICF2G630371956, BICF2S2356299, BICF2P526639, BICF2P154295, BICF2P412007, BICF2S23645462, BICF2G630373050, and BICF2P471347. The dog has an increased propensity for CCLR when five or more SNPs (or 10 or more, or 15 or more, or 20 or more) are detected in the dog's genomic DNA.

Also disclosed herein is a method for diagnosing propensity to non-contact cranial cruciate ligament rupture (CCLR) in a dog. Here, the method focuses on mutations in specific genes. The method comprises isolating genomic DNA from a dog. The DNA is then analyzed for single nucleotide polymorphisms occurring within, or in a genomic interval of about 2 Mb upstream or downstream of, at least one gene selected from the group consisting of CDH18, DPPA3, UBE2D1, ASS1, SPRED2, DLC1, DYSF, SCGB2, CHST2, SLC15A, ANO2, ERRFI1, SCGB2, and TRIM42. Again, the dog has an increased propensity for CCLR when five or more SNPs (or 10 or more, or 15 or more, or 20 or more) are detected in the dog's genomic DNA.

Also disclosed herein are kits for diagnosing the propensity to non-contact cranial cruciate ligament rupture (CCLR) in a dog. The kits comprise oligonucleotide probes or primers dimensioned and configured to bind selectively to single nucleotide polymorphism occurring within, or in a genomic interval of about 2 Mb upstream or downstream of at least one locus selected from the group consisting of BICF2P1126668, BICF2P260555, BICF2P599385, BICF2P1465216, BICF2S23135243, BICF2P170661, TIGRP2P78405, BICF2P890246, BICF2P401973, BICF2G630114782, BICF2G630815470, BICF2G630815474, BICF2S23448539, BICF2P1121006, BICF2G630371956, BICF2S2356299, BICF2P526639, BICF2P154295, BICF2P412007, BICF2S23645462, BICF2G630373050, and BICF2P471347. Instructions for use of the kit are typically included.

Numerical ranges as used herein are intended to include every number and subset of numbers contained within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, from 1 to 9, from 3.6 to 4.6, from 3.5 to 9.9, and so forth.

All references to singular characteristics or limitations of the present invention shall include the corresponding plural characteristic or limitation, and vice-versa, unless otherwise specified or clearly implied to the contrary by the context in which the reference is made. Unless otherwise stated, the indefinite articles "a" and "an" mean "one or more." When referring to a previously stated element, the definite article "the" does not limit the stated definition of "a" and "an," as being "one or more."

All combinations of method or process steps as used herein can be performed in any order, unless otherwise specified or clearly implied to the contrary by the context in which the referenced combination is made.

The methods and kits disclosed herein can comprise, consist of, or consist essentially of the essential elements and limitations described herein, as well as any additional or optional steps, ingredients, components, or limitations described herein or otherwise useful in gathering, preparing, and sequencing genomic DNA for analysis.

BRIEF DESCRIPTION OF THE DRAWINGS

FIG. 4 is a graph showing the distribution of the number of ACL rupture risk loci in case and control groups of Labrador Retriever dogs. The number of risk alleles in cases and controls is significantly different (P<2.2E-16). FIG. 5 is a graph depicting ACL rupture odds ratios of weighted genetic risk scores (wGRS) relative to the first quartile. Vertical bars represent the 95% confidence intervals. *Odds ratio is significantly different from the reference first quartile.

DETAILED DESCRIPTION

Figure 1:
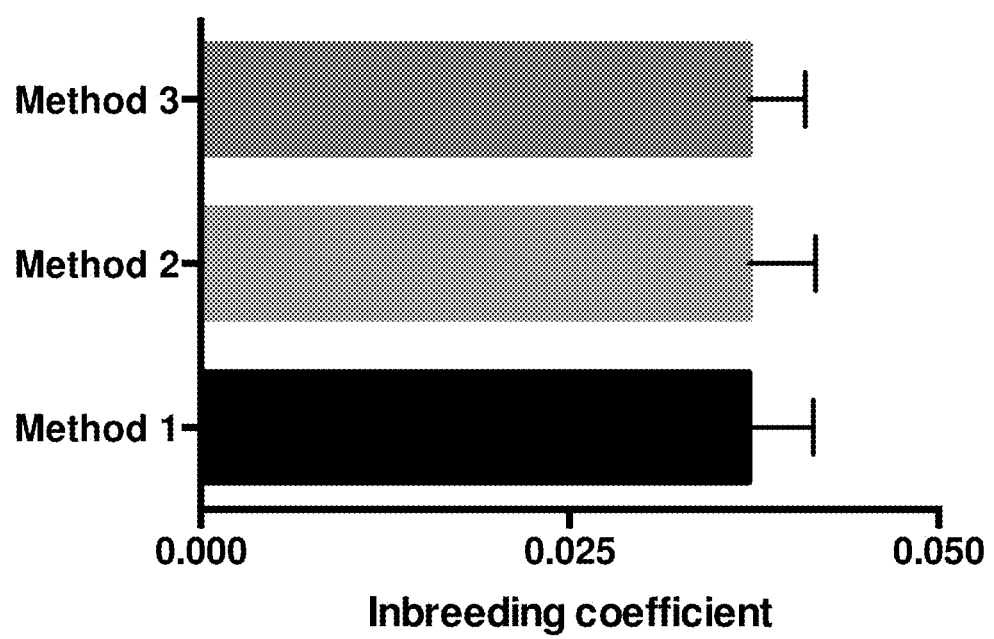
FIG. 1 is a graph showing that the Labrador Retriever is a dog breed with a relatively low amount of inbreeding. Whiskers represent the minimum and maximum values for each analysis method (n =237 dogs).

Abbreviations and Definitions:
CCLR: cranial cruciate ligament rupture (non-contact).
EDTA: Ethylenediaminetetraacetic acid.
GEMMA: Genome-wide efficient mixed model association.
GenABEL is an online project is to provide a free framework for collaborative, robust, transparent, and open source-based development of statistical genomics methodology. See http://www.genabel.org/.

GRAMMAR-Gamma is a genomic analysis program which is available through GenABEL. See also Svishcheva, G. R., Axenovich, T. I., Belonogova, N. M., van Duijn, C. M., and Aulchenko, Y. S. (2012) "Rapid variance components-based method for whole-genome association analysis," Nature Genetics 44:1166-1170.

GWAS: Genome-wide association study. A genome-wide association study is an analysis of genetic variation at specified loci in different individuals to see if any variant(s) is (are) associated with a phenotypic trait. As the name indicates, genetic markers across the complete genome of each individual test subject are tested to find genetic variations associated with a particular disease, in this case CCLR in dogs. Once new genetic associations are identified, the information is used to detect, treat and/or prevent the disease. Such studies are particularly useful in finding genetic variations that contribute to common, but complex diseases.

LD: Linkage disequilibrium. Linkage disequilibrium is the non-random association of alleles at two or more loci that descend from single, ancestral chromosomes.

MDS: multidimensional scaling.

MLM, LLM (synonymous): mixed linear model, linear mixed model, respectively.

P3D: Population parameters previously determined.

PLINK: PLINK is a free, open-source whole genome association analysis program that performs a range of large-scale genomic analyses in a computationally efficient manner. The PLINK software was developed (and continues to be refined) by Shaun Purcell and others at the Center for Human Genetic Research, Massachusetts General Hospital, and the Broad Institute of Harvard & MIT. PLINK v.1.9 is available online as of May 15, 2014 at http://pngu.mgh.harvard.edu/~purcell/plink/.

SNP: Single nucleotide polymorphism.

TASSEL: Trait analysis by association, evolution and linkage.

Unless otherwise noted, technical terms are used according to conventional usage. Definitions of common terms in genetics, genomics, and molecular biology may be found in Benjamin Lewin, "Genes V," published by Oxford University Press, 1994 (ISBN 0-19-854287-9) and Kendrew et al. (eds.), "The Encyclopedia of Molecular Biology," published by Blackwell Science Ltd., 1994 (ISBN 0-632-02182-9).

Canine Samples and Phenotyping:

DNA was isolated from client-owned Labrador Retrievers using blood or buccal swabs. A four-generation pedigree was collected from each dog to ensure purebred status and identify siblings, which were excluded from the GWAS. Each dog underwent an orthopaedic examination that included assessment of knee stability [Muir P. Physical examination of lame dogs. Comp Cont Ed Pract. Vet 1997; 19: 1149-1161]. Radiographs of the affected knee(s) were also assessed in cases. In addition, lateral weight-bearing knee radiographs [Kim S E, Lewis D D, Pozzi A, Seibert R L, Winter M D. Radiographic quantitative assessment of cranial tibial subluxation before and after tibial plateau leveling osteotomy in dogs. Am J Vet Res. 2011;72: 420-416] were made to screen phenotype-negative control dogs. While it is not possible to identify the cruciate ligaments radiographically in the dog, compression of the infrapatellar fat pad in the knee by synovial effusion and knee osteophytosis are degenerative changes typically associated with ACL rupture [Chuang C, Ramaker M A, Kaur S, Csomos R A, Kroner K T, Bleedorn J A, et al. Radiographic risk factors for contralateral rupture in dogs with unilateral cranial cruciate ligament rupture]. Dogs were considered cases if anterior translation of the tibia was detected clinically and radiographic signs were consistent with ACL rupture. Labrador Retrievers ≥8 years of age have less than a 6% chance of developing ACL rupture [Reif U, Probst C W. Comparison of tibial plateau angles in normal and cranial cruciate deficient stifles of Labrador retrievers. Vet Surg. 2003;32: 385-389]. Therefore, control dogs were ≥8 years of age with a normal orthopaedic clinical exam and normal knee radiographs. Habitual activity of each dog was documented using a questionnaire.

Genome-Wide Association:

Genome-wide SNP genotyping was performed in 98 cases and 139 controls using the Illumina CanineHD BeadChip, which genotypes 173,662 SNPs evenly spaced across the genome. Data underwent quality control filtering using PLINK [Chang C C, Chow C C, Tellier L C A M, Vattikuti S, Purcell S M, Lee J J. Second-generation PLINK: rising to the challenge of larger and richer datasets. GigaScience. 2015;4:7]. All samples had a genotyping call rate of ≥95%. 49,859 SNPs were excluded because minor allele frequency (MAF) was ≤0.05 and 7,468 SNPs were excluded because of a low genotyping rate (≤95%). 153 SNPs were excluded because of deviation from Hardy-Weinberg equilibrium at P<1E-07. 118,992 SNPs were used for further analysis.

To account for ancestral population structure and family relatedness in the study dogs, single marker linear mixed model (LMM) analysis was performed using GCTA (Genome-wide Complex Trait Analysis) [Yang K, Lee S H, Goddard M E, Visscher. GCTA: A tool for genome-wide complex trait analysis. Am J Hum Genet. 2011;88: 76-82] and GEMMA (Genome-wide Efficient Mixed Model Association) [Zhou X, Stephens M. Genome-wide efficient mixed-model analysis for association studies. Nat Genet. 2012;44: 821-824], software tools optimized for complex trait GWAS. Penalized Unified Multiple-locus Association (PUMA), in which all SNPs are analyzed together, was also used to aid detection of weaker associations often found in complex traits [Hoffman G E, Logsdon B A, Mezey J G. PUMA: A unified framework for penalized multiple regression analysis of GWAS data. PLoS Comput Biol. 2013;9: e1003101]. We used logistic regression and a 2D-MCP penalty for this analysis [Hoffman G E, Logsdon B A, Mezey J G. PUMA: A unified framework for penalized multiple regression analysis of GWAS data. PLoS Comput Biol. 2013;9: e1003101; Zhang C H. Nearly unbiased variable selection under minimax concave penalty. Ann Stat. 2010;38: 894-942]. In the PUMA analysis, the first 20 eigenvectors were used as covariates in the association analysis to correct for population structure. Eigenvectors were obtained by principal component analysis using GCTA. Because neutering has a significant effect on risk of ACL rupture, it was included as a covariate with the GEMMA, GCTA, and PUMA analyses.

Genome-Wide Significance:

We defined genome-wide significance using permutation testing. Use of a Bonferroni correction for the number of SNPs tested is too conservative in dog breeds, as extensive LD means that SNPs are often inherited in haplotype blocks [Lindblad-Toh K, Wade C M, Mikkelsen T S, Karlsson E K, Jaffe D B, Kamal M, et al. Genome sequence, comparative analysis, and haplotype structure of the domestic dog. Nature. 2005;438: 803-819]. We defined genome-wide significance by randomly permuting the phenotypes and re-running the GWAS LMM 1,000 times. Genome-wide significance was defined by identifying the 5% quantile of the set of minimum P-values from the GWAS permutations. Additionally, we calculated the number of haplotype blocks in the Labrador Retriever SNP data using PLINK, using LD windows of 500 kb, 1 Mb, and 5 Mb and used the number of haplotype blocks to estimate genome-wide significance by Bonferroni correction of P<0.05. To facilitate further dissection of genetic variants associated with the ACL phenotype, we also identified a larger set of candidate ACL rupture regions at P<5E-04 [Karlsson E K, Sigurdsson S, Ivansson E, Thomas R, Elvers I, Wright J, et al. Genome-wide analyses implicate 33 loci in heritable dog osteosarcoma, including regulatory variants near CDKN2A/B. Genome Biol. 2013;14: R132]. Although some of the regions included may not be true associations, this would likely weaken rather than strengthen the gene set and pathway analyses, leading to false negatives rather than false positives.

Defining Associated Loci in the Genome:

Linkage-disequilibrium (LD) clumping using PLINK was used to define regions of association with the ACL rupture trait from the GWAS results. LD clumping defined regions around SNPs associated at P<5E-04. Regions within 1 Mb of the index SNP ($r^2>0.8$ and P<0.01). We also used GCTA to explain the phenotype variance explained by the associated loci, which were defined as SNPs with $r^2>0.2$ within 5 Mb of the peak SNP in each locus [Tang R, Noh H J, Wang D, Sigurdsson S, Swofford R, Perlosko M, et al. Candidate genes and functional noncoding variants identified in a canine model of obsessive-compulsive disorder. Genome Biol. 2014;15: R25].

For complex trait GWAS with a large number of risk loci, loci that are not discovered are expected to have smaller effect sizes in a second generation GWAS, because those with larger effect sizes will have been identified in the first round of GWAS. To estimate the number of risk loci that are likely associated with ACL rupture, we used INPower. Odds ratios were corrected for the winner's curse before INPower analysis was performed. See Park J-HM, Wacholder S, Gail M, Peters U, Jacobs K B, Chanock S J, et al. Estimation of effect size distribution from genome-wide association studies and implications for future discoveries. Nat Genet. 2010;42: 570-575 and Ghosh A, Zou F, Wright F A. Estimating odds ratios in genome scans: An approximate conditional likelihood approach. Am J Human Genet. 2008;82: 1064-1074.

Genetic Risk Score Computation:

Two approaches were used to calculate the genetic risk scores (GRS), a simple risk alleles count method (cGRS) and a weighted method (wGRS) [Chen H, Poon A, Yeung C, Helms C, Pons J, Bowcock A M, et al. A genetic risk score combining ten psoriasis risk loci improves disease prediction. PLoS One. 2011;6: e19454]. The wGRS weights each risk allele by the logarithm odds ratio (Log(OR)) for that allele. The wGRS is a linear combination of the number of risk alleles weighted by the Log(OR) as coefficients. The Mann-Whitney U test was used to compare cGRS scores for each LMM in case and control groups. To estimate the total risk captured by the genetic risk scoring for each LMM, we calculated the odds ratios according to the wGRS quartiles. We also measured the discriminative power attributable to the GRS by plotting receiver operating characteristic (ROC) curves and calculated the area under the curve (AUC) for the Labrador Retriever case and control dogs. AUC 95% confidence intervals were calculated using 2000 stratified bootstrap replicates. An R software package (http://www.r-project.org/) was used for these analyses.

Pathway Analysis:

Pathway analysis was performed with two methods. DAVID [Huang D W, Sherman B T, Lempicki R A. Systematic and integrative analysis of large gene lists using DAVID bioinformatics resources. Nat Protoc. 2009;4: 44-57] analyses were run on the ACL rupture loci identified from our GWAS. ACL rupture loci were transposed to CanFam 3.1 coordinates (genome.ucsc.edu/cgi-bin/hgLiftOver) with 500 kB flanks added to the start and end and gene size correction turned on [Tang R, Noh H J, Wang D, Sigurdsson S, Swofford R, Perlosko M, et al. Candidate genes and functional noncoding variants identified in a canine model of obsessive-compulsive disorder. Genome Biol. 2014;15: R25]. A list of genes from the liftover coordinates was then analyzed. Probability values were evaluated after Benjamini correction with DAVID.

Pathway analysis with INRICH was performed on canFam2 intervals using a map file lifted over from the canFam3.1 Broad Improved Canine Annotation catalog (UCSC Genome Browser) [Lee P H, Dushlaine C O, Thomas B, Purcell S M. INRICH: interval-based enrichment analysis for genome-wide association studies. Bioinformatics. 2012; 28: 1797-1799]. We used 1,000,000 permutations matched for region size, SNP density, and gene number. INRICH reports significance for each gene set and the experiment-wide significance, correcting for the number of gene sets ($P_{corr}$). We considered $P_{corr}$<0.05 to be significant. We tested gene sets from the KEGG (Kyoto Encyclopedia of Genes and Genomes), Gene Ontology, and MSigDB (Molecular Signatures Database).

Heritability Estimation:

Narrow sense heritability was estimated from SNPs using the BGLR statistical package [Pérez P, de los Campos G. Genome-wide regression and prediction with the BGLR statistical package. Genetics. 2014;198: 483-495]. SNPs with missing genotypes were filtered out using PLINK. Heritability estimation was performed using SNPs. A genomic best linear unbiased prediction (GBLUP) model was fitted using a SNP-derived genomic relationship matrix using a non-parametric reproducing kernel Hilbert spaces (RKHS) method as described in Pérez (2014). Broad sense heritability was also estimated using a data matrix prepared from pedigrees. To fit the model, 30,000 iterations of the Gibbs sampler were used with burn-in of 5,000 iterations. A correction factor was used to transform the heritability estimate on the observed scale from the regression model to the liability scale for a binary trait [Zhou X, Caronetto P, Stephens M. Polygenic modeling with Bayesian sparse linear mixed models. PLoS Genetics. 2013;9: e1003264] and a population prevalence of 0.0579 [Witsberger T H, Villamil J A, Schultz L G, Hahn A W, Cook J L. Prevalence of and risk factors for hip dysplasia and cranial cruciate ligament deficiency in dogs. J Am Vet Med Assoc. 2008;232: 1818-1824] was used for this correction.

Linkage Disequilibrium Analysis:

After obtaining the results from each MLM, LD-based clumping was calculated in PLINK to define associated regions in LD with the most significant SNPs ($r^2$>0.5, within 2 Mb of the associated SNP). These settings were modified from another GWAS for a complex trait in dogs. [Karlsson et al. (2013). Genome-wide analyses implicate 33 loci in heritable dog osteosarcoma, including regulatory variants near CDKN2A/B. *Genome Biology*. 14:R132.] These regions were then investigated with the NCBI Canine Genome Map Viewer to identify nearby genes using the CanFam 3.0 reference sequence.

GWAS Population of Labrador Retrievers:

We genotyped 237 Labrador Retrievers using the Illumina CanineHD BeadChip, removing SNPs with call rates of <95%. No dogs were removed after SNP filtering. The final dataset contained 118,992 SNPs from 98 cases and 139 phenotype-negative controls. Median inbreeding coefficient was 0.025 (FIG. 1). The ratio of females to males in the case and control groups was 0.92 and 0.83 respectively. Of the 114 females, 99 were ovariohysterectomized (0.87). Of the 123 males, 96 were castrated (0.78). Mean age of the dogs in the case and control groups was 6.0±2.5 years and 10.4±1.7 years, respectively.

Figure 2:
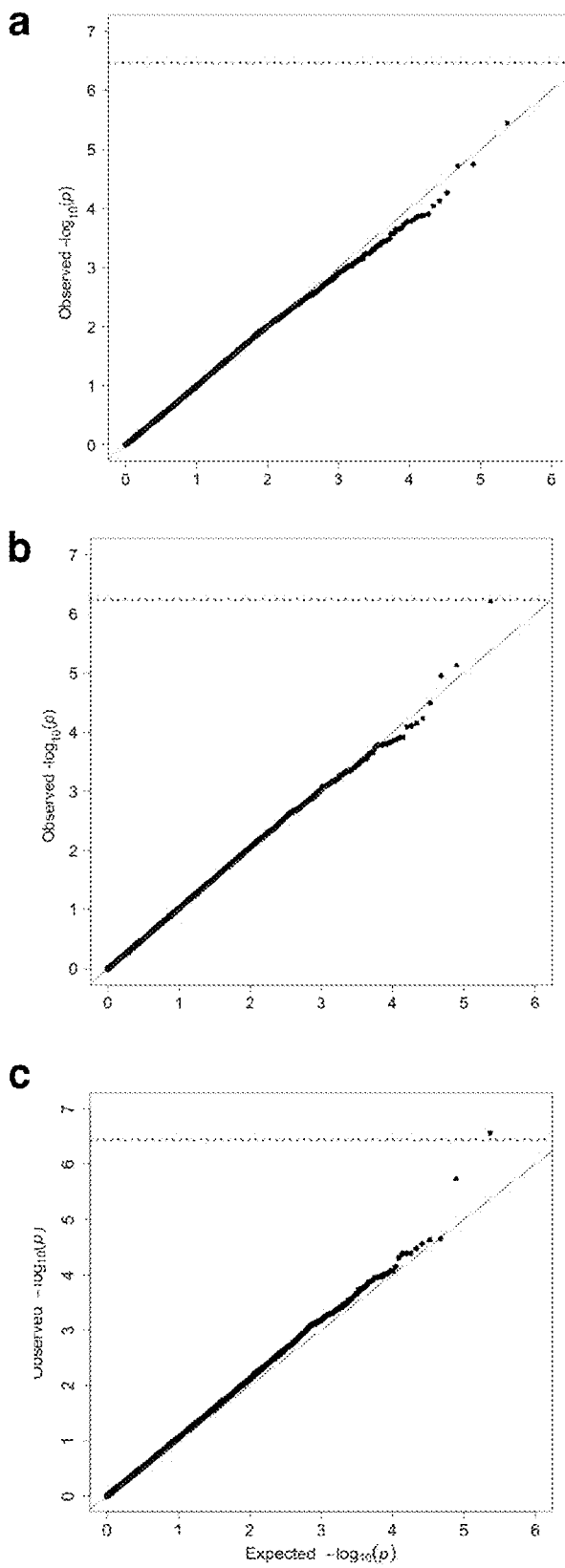
FIG. 2 is a series of graphs demonstrating that linear mixed model GWAS corrects for population structure and identifies 98 ACL associated loci explaining a large proportion of phenotypic variance. For each linear mixed model (LMM), the QQ plots show no evidence of population stratification relative to the expected distribution. Permutation testing with each model determined genome-wide significance at panel (a) P<3.63E-7 for GCTA (Genome-wide Complex Trait Analysis), $\lambda=0.987$; panel (b) P<6.097E-7 for GEMMA (Genome-wide Efficient Mixed Model Association), $\lambda=0.994$; and panel (c) P<4.01E-7 for PUMA (Penalized Unified Multiple-locus Association, $\lambda=1.012$. The plots represent analysis of 118,992 SNPs from 98 cases and 139 phenotype-negative controls. Panel (d): with GCTA, 36 loci have P<5E-4, with the most significant locus located in CFA 26, which did not meet genome-wide significance defined by minimum p-values from permutation testing. Panel (e): with GEMMA, 47 loci have P<5E-4, with the locus on CFA 26 meeting genome-wide significance defined by minimum p-values from permutation testing. Panel (f): with PUMA, 65 loci were significant at P<5E-4 and the locus on CFA 26 exceeded genome-wide significance defined by minimum p-values from permutation testing.
Figure 2:
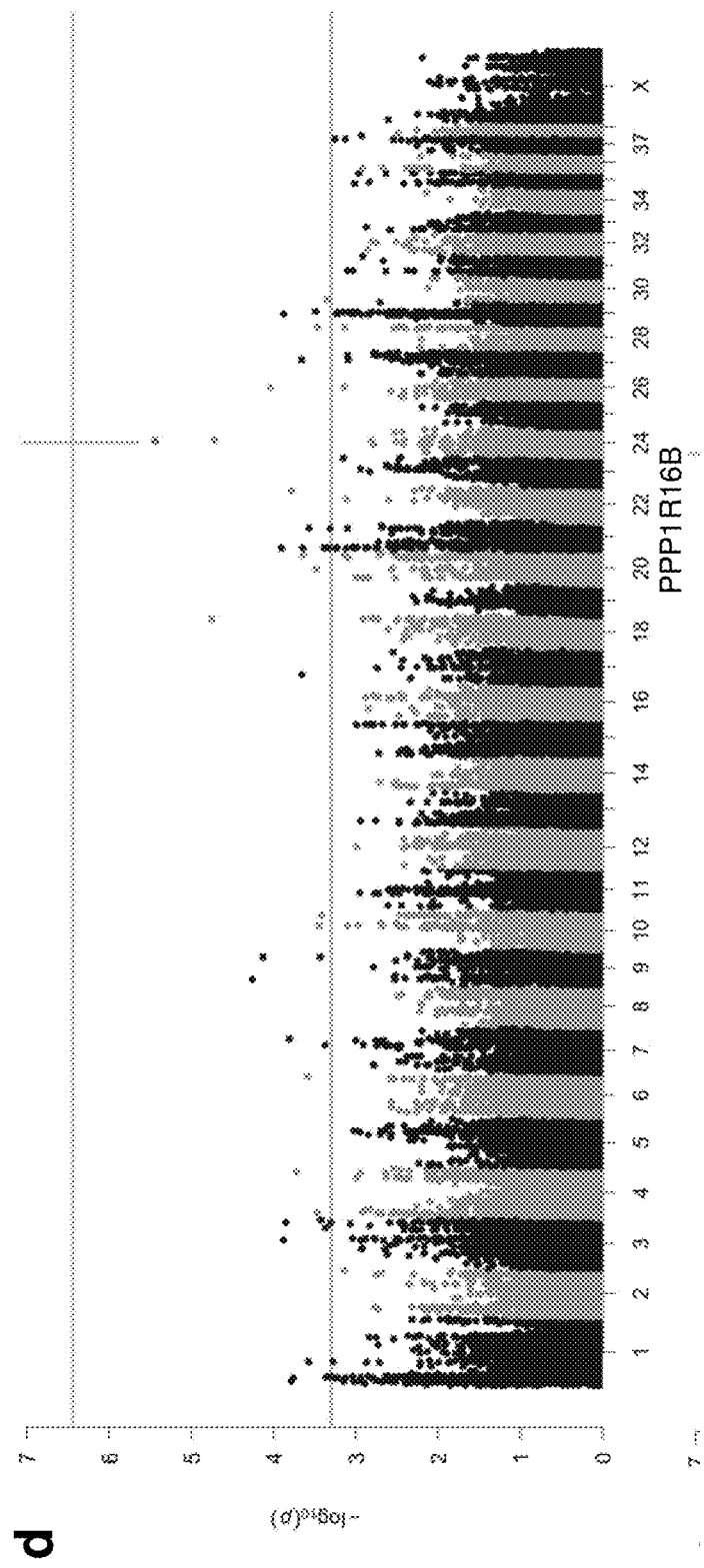
Figure 2:
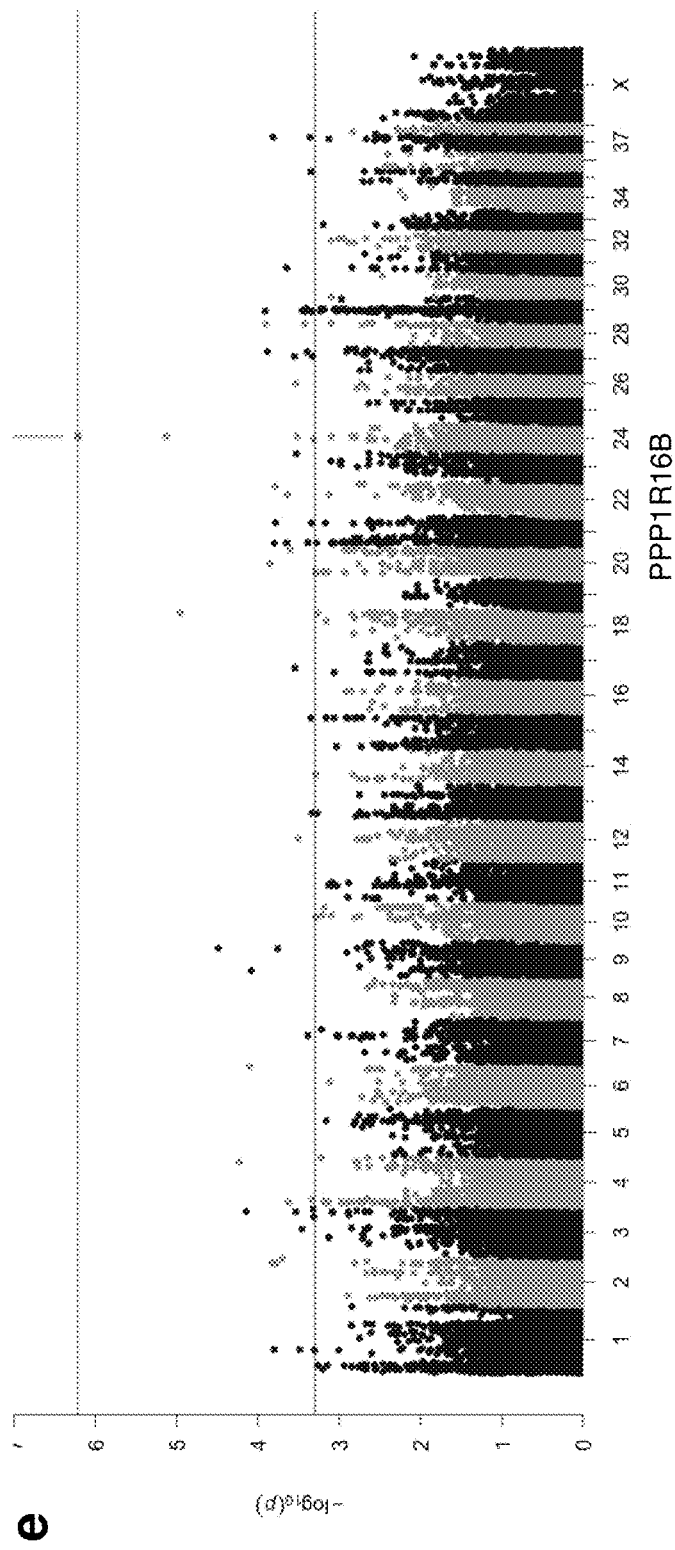
Figure 2:
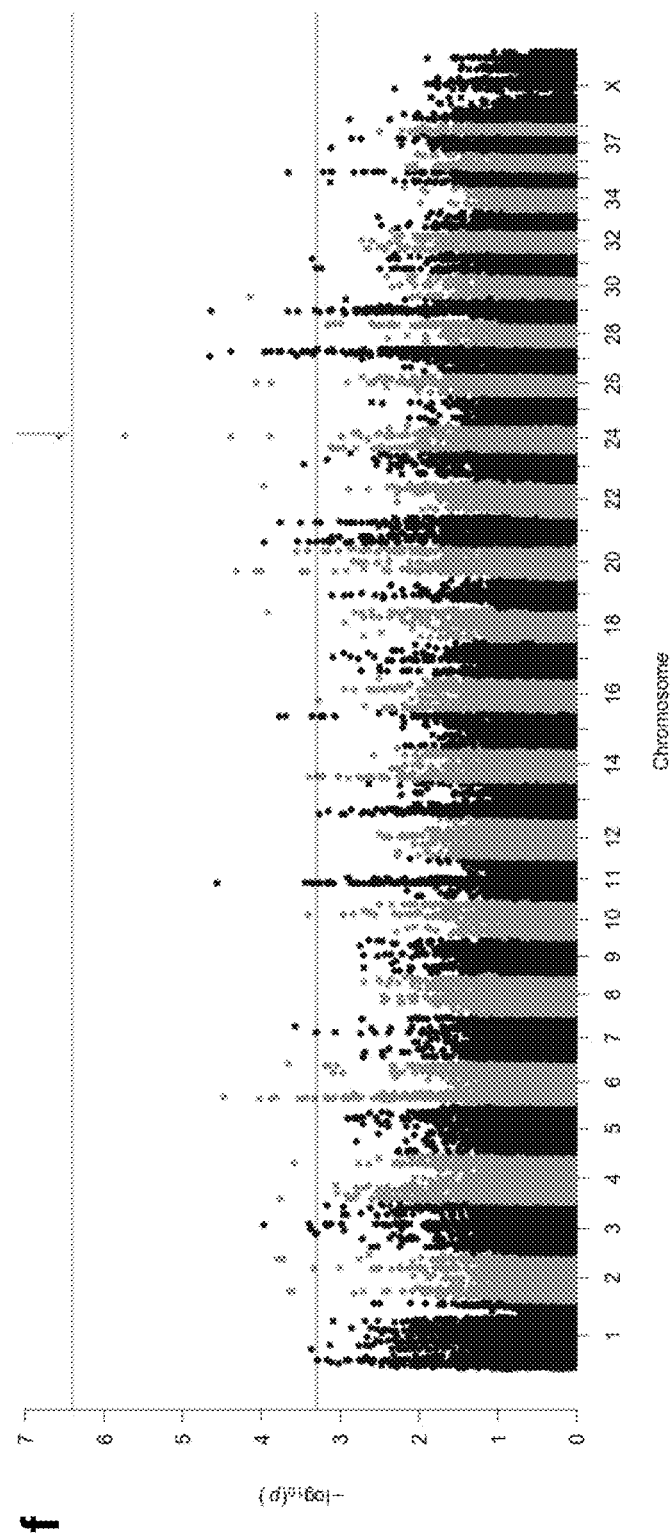

GWAS Identifies 98 Regions Associated with Anterior Cruciate Ligament Rupture:

We tested for association between ACL rupture and SNPs with a MAF >0.05 in the Labrador Retriever breed, controlling for cryptic relatedness and population structure using LMM analysis with three programs, including a penalized multiple regression method for improved detection of weak associations. We identified all SNPs with either significant association based on analysis of 1,000 random phenotype permutations to define genome-wide significance (P<1.549E-06 for GCTA, P<6.097E-07 for GEMMA and P<4.35E-07 for PUMA) or suggestive association (P<5.00E-04; FIG. 2) and defined regions of associated using linkage disequilibrium. See Tables 1 and 2. Control dogs were considered phenotype-negative because of the selection criteria used for recruitment. We identified 21,713; 21,754; and 21,861 haplotype blocks in the Labrador Retriever genome with LD windows of 5 Mb, 1 Mb, and 5 kb respectively, yielding a genome-wide significance estimate of P<2.29E-06 to P<2.30E-06.

TABLE 1

Anterior cruciate ligament rupture associated loci identified by GWAS in the Labrador Retriever, a dog breed with a high disease prevalence

| SNP | chr | Position | P | LMM | Risk allele | f(A) | f(U) | OR | Region start-end | Size (kB) | Genes |
| --- | --- | --- | --- | --- | --- | --- | --- | --- | --- | --- | --- |
| BICF2G630500368 | 24 | 30241088 | 2.76E-07 | 1, 2, 3 | G | 0.83 | 0.66 | 2.56 | 30241088-30245795 | 5 | BPI, LBP, RALGAPB, ADIG, ARHGAP40, SLC32A1, ACTR5, PP1R16B, FAM83D, DHX35 |
| BICF2P1121006 | 18 | 54279578 | 1.11E-05 | 1, 2, 3 | A | 0.63 | 0.42 | 2.28 | No LD | | Many (30 genes) |
| BICF2S2356299 | 27 | 30557856 | 2.21E-05 | 2, 3 | A | 0.43 | 0.27 | 2.03 | No LD | | None |
| BICF2P483191 | 29 | 21601273 | 2.31E-05 | 1, 2, 3 | C | 0.73 | 0.51 | 2.54 | No LD | | SULF1 SLCO5A1, PRDM14, NCOA2, TRAM1 |
| BICF2P50610 | 11 | 32270617 | 2.75E-05 | 3 | A | 0.29 | 0.19 | 1.7 | 31939564-32270617 | 331 | C11H9orf123, PTPRD |
| BICF2P890246 | 9 | 53427907 | 3.23E-05 | 1, 2 | A | 0.16 | 0.36 | 2.99 | 53427907-53432248 | 4 | Many (26 genes) |
| BICF2S23324965 | 6 | 14077648 | 3.36E-05 | 3 | G | 0.68 | 0.60 | 1.42 | 14077648-14092057 | 14 | NPTX2, BAIAP2L1, BRI3, TECPR1, BHLHA15, LMTK2, CCZ1, RSH10B, |

TABLE 1-continued

Anterior cruciate ligament rupture associated loci identified by GWAS in the Labrador Retriever, a dog breed with a high disease prevalence

| SNP | chr | Position | P | LMM | Risk allele | f(A) | f(U) | OR | Region start-end | Size (kB) | Genes |
|---|---|---|---|---|---|---|---|---|---|---|---|
| BICF2P544126 | 24 | 29772193 | 4.09E−05 | 3 | G | 0.94 | 0.87 | 2.28 | 29772193-29794411 | 22 | PMS2, AIMP2, ANKRD61, EIF2AK1, USP42, CYTH3, CTNNBL1, VSTM2L, TTI1, RPRD1B, TGM2, KIAA1755 |
| BICF2P526639 | 27 | 39217437 | 4.12E−05 | 2, 3 | G | 0.23 | 0.12 | 2.18 | 39211186-39217437 | 6 | A2M |
| BICF2P1462185 | 20 | 15053718 | 4.89E−05 | 3 | A | 0.85 | 0.74 | 1.90 | 14838270-15053718 | 215 | EDEM1, ARL8B |
| BICF2P1208798 | 9 | 12671217 | 5.49E−05 | 1, 2 | G | 0.56 | 0.36 | 2.27 | No LD | | EFCAB13, ITGB3, MYL4, CDC27, KANSL1, MAPT, SPPL2C, CRHR1, NSF, WNT3 |
| BICF2G630175389 | 4 | 84260906 | 5.87E−05 | 1, 2 | A | 0.83 | 0.68 | 2.28 | No LD | | CDH10 |
| BICF2S24415473 | 3 | 86974042 | 7.07E−05 | 1, 2 | G | 0.40 | 0.26 | 1.97 | 86948527-86974042 | 26 | STIM2, PGM2, RELL1, C3H4orf19, NWD2 |
| BICF2G630412697 | 30 | 3126573 | 7.22E−05 | 1, 3 | G | 0.96 | 0.86 | 4.23 | No LD | | COR4F22P, COR4F25, COR4F24P, COR4T2P |
| BICF2P498515 | 6 | 75848537 | 7.89E−05 | 1, 2, 3 | A | 0.16 | 0.06 | 3.11 | No LD | | LRRIQ3 |
| BICF2P792911 | 26 | 22894961 | 8.55−05 | 1, 2, 3 | G | 0.44 | 0.27 | 2.14 | No LD | | TPST2, CRYBB1, CRYBB4 |
| BICF2G630810143 | 6 | 11130832 | 9.46E−05 | 3 | A | 0.44 | 0.32 | 1.72 | 11130832-11177149 | 46 | DTX2, UPK3B, UPK3BL, RASA4, LRWD1, ALKBH4, ORAI2, PRKRIP1, SH2B2, CUX1, MYL10, COL26A1, RABL5, RIS1, CLDN15, ZNHIT1, PLOD3 |
| BICF2P564273 | 3 | 55250188 | 1.07E−04 | 1, 2, 3 | A | 0.70 | 0.52 | 2.16 | No LD | | ACAN, HAPLN3, MFGE8, ABHD2, RLBP1, FANCI, POLG, TRNAR-UCG, RHCG, TICRR, KIF7, PLIN1, PEX11A, WDR93, MESP1, MESP2, ANPEP, AP3S2, ARPIN |
| TIGRP2P297337 | 22 | 58201452 | 1.08E−04 | 1, 2, 3 | A | 0.44 | 0.27 | 2.2 | No LD | | EFNB2, ARGLU1 |
| BICF2G630658881 | 21 | 7582214 | 1.09E−04 | 1, 2, 3 | G | 0.49 | 0.32 | 2.12 | 7581714-8383209 | | JRKL, CCDC82, MAML2, MTMR2, CEP57, FAM76B, SESN3 |

Note:
OR odds ratio calculated from PLINK. LMM Linear mixed model 1 - GCTA, 2 - GEMMA, 3 - PUMA.
Data represent the twenty most significant loci of 98 associations with canine ACL rupture.
SNP position and genomic regions are based on CanFam 2.0.
Genes lists were derived from the SNP locus or LD block with 500 kb flanking regions.

TABLE 2

Anterior cruciate ligament rupture associated SNPs identified by GWAS in the Labrador Retriever, a dog breed with a high disease prevalence

| SNP | chr | Position | P | LMM | Risk Allele | f(A) | f(U) | OR | Region start-end | Genes |
|---|---|---|---|---|---|---|---|---|---|---|
| BICF2G630709791 | 1 | 10788643 | 1.64E−04 | 1 | C | 0.30 | 0.16 | 2.18 | 10788643-11025688 | RTTN, CD226, DOK6 |
| BICF2S23147946 | 1 | 17290917 | 1.74E−04 | 1 | G | 0.28 | 0.15 | 2.19 | No LD | BCL2, PHLPP1, ZCCHC2, TNFRSF11A, KIAA1468, PPIAP1, PIGN |
| BICF2P181859 | 1 | 17840093 | 4.32E−04 | 1 | A | 0.21 | 0.09 | 2.60 | No LD | ZCCHC2, TNFRSF11A, KIAA1468, PPIAP1, PIGN, CDH20 |
| BICF2G630712921 | 1 | 19148000 | 4.94E−04 | 1 | G | 0.46 | 0.32 | 1.87 | 18645187-19148000 | CDH20, MC4R, PMAIP1, CCBE1 |
| BICF2G630713147 | 1 | 19274346 | 4.93E−04 | 1 | A | 0.37 | 0.24 | 1.83 | 19253280-19274346 | MC4R, PMAIP1, CCBE1 |
| BICF2P818099 | 1 | 39021948 | 4.29E−04 | 3 | G | 0.65 | 0.54 | 1.55 | No LD | SF3B5, STX11, TRNAL-UAA, UTRN |
| BICF2S23638642 | 1 | 45229667 | 4.95E−04 | 2 | G | 0.18 | 0.07 | 3.07 | No LD | AKAP12, ZBTB2, RMND1, ARMT1, |

TABLE 2-continued

Anterior cruciate ligament rupture associated SNPs identified by GWAS in the Labrador Retriever, a dog breed with a high disease prevalence

| SNP | chr | Position | P | LMM | Risk Allele | f(A) | f(U) | OR | Region start-end | Genes |
|---|---|---|---|---|---|---|---|---|---|---|
| BICF2P206910 | 1 | 46405864 | 3.25E−04 | 2 | C | 0.14 | 0.04 | 4.05 | 46405864-46443183 | CCDC170, ESR1, SYNE1 MYCT1, VIP, |
| BICF2S22959529 | 1 | 46443183 | 1.58E−04 | 1, 2 | C | 0.14 | 0.03 | 4.78 | | FBXO5, MTRF1L, RGS17 |
| BICF2P1054044 | 2 | 20002181 | 2.28E−04 | 3 | G | 0.85 | 0.77 | 1.74 | No LD | MTPAP, MAP3K8, LYZL1, TRNAK-CUU, BAMBI, WAC |
| BICF2S23533020 | 2 | 20501149 | 2.47E−04 | 3 | G | 0.92 | 0.84 | 2.33 | 20288541-20501149 | LYZL1, TRNAK-CUU, BAMBI, WAC, MPP7 |
| BICF2P720951 | 2 | 62500174 | 4.61E−04 | 3 | A | 0.26 | 0.16 | 1.82 | 62252040-62500174 | GPR114, CCDC102A, DOK4, POLR2C, COQ9, CIAPIN1, CCL17, CX3CL1, CCL22, TRNAL-CAG, PLLP, ARL2BP, RSPRY1, FAM192A, CPNE2, NLRC5, HERPUD1, SLC12A3, NUP93, MT2A, MT-III, MT4, BBS2, OGFOD1, NUDT21, AMFR, GNAO1 |
| TIGRP2P31530 | 2 | 80046637 | 1.65E−04 | 2, 3 | G | 0.67 | 0.55 | 1.69 | 80046637-80079758 | C1QB, C1QC, C1QA, EPHA8, ZBTB40, WNT4, CDC42, CELA3B, HSPG2, LDLRAD2, USP48, RAP1GAP, ALPL |
| BICF2P247448 | 2 | 80068322 | 1.48E−04 | 2, 3 | G | 0.68 | 0.55 | 1.67 | | |
| BICF2P1066899 | 2 | 80079758 | 1.65E−04 | 2, 3 | A | 0.67 | 0.55 | 1.69 | | |
| BICF2G630464857 | 2 | 87862734 | 2.00E−04 | 2 | G | 0.14 | 0.04 | 3.69 | No LD | C2H1orf167, AGTRAP, DRAXIN, MAD2L2, FBXO6, FBXO44, FBXO2, PTCHD2, UBIAD1, MTOR, ANGPTL7, EXOSC10, SRM, MASP2, TARDBP, CASZ1, PEX14, DFFA, APITD1, PGD |
| BICF2G630108404 | 3 | 39424250 | 4.96E−04 | 3 | G | 0.24 | 0.13 | 2.06 | 39424250-39517119 | NDN, MKRN3, CHRNA7 |
| BICF2S23148483 | 3 | 39469011 | 4.96E−04 | 3 | G | 0.24 | 0.13 | 2.06 | | |
| BICF2P866702 | 3 | 39517119 | 4.96E−04 | 3 | A | 0.24 | 0.13 | 2.06 | | |
| BICF2P1109077 | 3 | 48873558 | 4.26E−04 | 3 | G | 0.80 | 0.67 | 1.90 | 48873558-48880579 | MCTP2 |
| BICF2P1431921 | 3 | 48878860 | 4.26E−04 | 3 | G | 0.80 | 0.67 | 1.90 | | |
| BICF2P241884 | 3 | 48880579 | 4.26E−04 | 3 | G | 0.80 | 0.67 | 1.90 | | |
| BICF2P564273 | 3 | 55250188 | 1.07E−04 | 1, 2, 3 | A | 0.70 | 0.52 | 2.16 | No LD | ACAN, HAPLN3, MFGE8, ABHD2, RLBP1, FANCI, POLG, TRNAR-UCG, RHCG, TICRR, KIF7, PLIN1, PEX11A, WDR93, MESP1, MESP2, ANPEP, AP3S2, ARPIN |
| TIGRP2P46522 | 3 | 57698908 | 4.01E−04 | 3 | C | 0.70 | 0.54 | 1.91 | 57660110-57698908 | PDE8A, RPS17, CPEB1, AP3B2, FSD2, WHAMM, HOMER2, FAM103A1, C3H5orf40, BTBD1, TM6F1, HDGFRP3, BNC1, SH3GL3 |
| BICF2G630349775 | 3 | 77625147 | 4.26E−04 | 1, 2 | A | 0.18 | 0.07 | 2.90 | No LD | TBC1D1, PGM2, RELL1, C3H4orf19, NWD2 |
| BICF2S2342150 | 3 | 86948527 | 2.91E−04 | 1, 2 | A | 0.40 | 0.27 | 1.83 | 86948527-86974042 | STIM2, TBC1D19, CCKAR, SMIM20, SEL1L3 |
| BICF2S24415473 | 3 | 86974042 | 7.07E−05 | 1, 2 | G | 0.40 | 0.26 | 1.97 | | |

TABLE 2-continued

Anterior cruciate ligament rupture associated SNPs identified by GWAS in the Labrador Retriever, a dog breed with a high disease prevalence

| SNP | chr | Position | P | LMM | Risk Allele | f(A) | f(U) | OR | Region start-end | Genes |
|---|---|---|---|---|---|---|---|---|---|---|
| BICF2G630359517 | 3 | 91944314 | 3.77E−04 | 1, 2 | C | 0.51 | 0.36 | 1.82 | No LD | KCNIP4, PACRGL, SLIT2 |
| BICF2G63058646 | 4 | 9120668 | 1.76E−04 | 1, 2, 3 | G | 0.13 | 0.04 | 3.71 | No LD | SLC35F3, KCNK1, KIAA1804, PCNXL2 |
| BICF2P295392 | 4 | 14536870 | 4.61E−04 | 2 | G | 0.11 | 0.04 | 3.07 | No LD | BICC1, PHYHIPL, FAM13C |
| BICF2G630168473 | 4 | 74924050 | 2.60E−04 | 3 | G | 0.30 | 0.18 | 1.96 | No LD | NUP155, C4H5orf42, NIPBL, SLC1A3 |
| BICF2G630175389 | 4 | 84260906 | 5.87E−05 | 1, 2 | A | 0.83 | 0.68 | 2.28 | No LD | CDH10 |
| BICF2G630810143 | 6 | 11130832 | 9.46E−05 | 3 | A | 0.44 | 0.32 | 1.72 | 11130832-11177149 | DTX2, UPK3B, UPK3BL, RASA4, LRWD1, ALKBH4, ORAI2, PRKRIP1, SH2B2, CUX1, MYL10, COL26A1, RABL5, FIS1, CLDN15, ZNHIT1, PLOD3 |
| BICF2G630810159 | 6 | 11177149 | 9.46E−05 | 3 | A | 0.44 | 0.32 | 1.72 | | |
| BICF2G630810173 | 6 | 11181920 | 1.33E−04 | 3 | G | 0.61 | 0.51 | 1.50 | 11035074-11181920 | SRCRB4D, ZP3, MOGAT3, NAT16 |
| BICF2P170661 | 6 | 11439931 | 3.39E−04 | 3 | A | 0.31 | 0.22 | 1.57 | No LD | VGF, AP1S1, SERPINE1, TRIM56, ACHE, UFSP1, SRRT, TRIP6, SLC12A9, EPHB4 |
| BICF2P1354767 | 6 | 11462695 | 3.02E−04 | 3 | G | 0.48 | 0.38 | 1.53 | 11106977-11462695 | None |
| BICF2P205255 | 6 | 11484772 | 4.75E−04 | 3 | G | 0.54 | 0.45 | 1.43 | No LD | ZAN |
| BICF2P1358119 | 6 | 13131171 | 3.74E−04 | 3 | C | 0.44 | 0.34 | 1.54 | 13131171-13182379 | AZGP1, GJC3, TRIM4, VN2R301P, CYP3A26, CYP3A4, OR0C09, ZSCAN25, FAM200A, ZKSCAN5, ZNF789, ZNF394, TRNAW-CCA, CPSF4, PTCD1, BUD31, PDAP1, ARPC1B, ARPC1A, MYH16, KPNA7, SMURF1, TRRAP, TMEM130 |
| BICF2S23324965 | 6 | 14077648 | 3.36E−05 | 3 | G | 0.68 | 0.60 | 1.42 | 14077648-14092057 | NPTX2, BAIAP2L1, BRI3, TECPR1, BHLHA15, LMTK2, CCZ1, RSPH10B, PMS2, AIMP2, ANKRD61, EIF2AK1, USP42, CYTH3 |
| BICF2S22961650 | 6 | 14092057 | 1.53E−04 | 3 | G | 0.68 | 0.61 | 1.35 | | |
| BICF2P498515 | 6 | 75848537 | 7.89E−05 | 1, 2, 3 | A | 0.16 | 0.06 | 3.11 | No LD | LRRIQ3 |
| BICF2P1072682 | 7 | 53407178 | 4.09E−04 | 1, 2, 3 | C | 0.28 | 0.14 | 2.42 | No LD | None |
| BICF2P1090079 | 7 | 64389761 | 1.56E−04 | 1, 3 | C | 0.47 | 0.31 | 1.94 | No LD | CDH2, CHST9 |
| BICF2P1208798 | 9 | 12671217 | 5.49E−05 | 1, 2 | G | 0.56 | 0.36 | 2.27 | No LD | EFCAB13, ITGB3, MYL4, CDC27, KANSL1, MAPT, SPPL2C, CRHR1, NSF, WNT3 |
| BICF2P890246 | 9 | 53427907 | 3.23E−05 | 1, 2 | A | 0.16 | 0.36 | 2.99 | 53427907-53432248 | KCNT1, SOHLH1, LCN9, GLT6D1, LCN1, ABO, SURF6, MED22, RPL7A, SURF1, SURF2, SURF4, C9H9orf96, REXO4, ADAMTS13, CACFD1, SLC2A6, TMEM8C, ADAMTSL2, FAM163B, DBH, SARDH, VAV2, BRD3, WDR5, RXRA |
| BICF2P139678 | 9 | 53432248 | 1.75E−04 | 1, 2 | A | 0.83 | 0.65 | 2.71 | | |
| BICF2S23113199 | 10 | 46246942 | 3.57E−04 | 1, 3 | A | 0.63 | 0.46 | 1.95 | No LD | AFF3, REV1, EIF5B, TXNDC9, LYG1, LYG2, MRPL30, |

TABLE 2-continued

Anterior cruciate ligament rupture associated SNPs identified by GWAS in the Labrador Retriever, a dog breed with a high disease prevalence

| SNP | chr | Position | P | LMM | Risk Allele | f(A) | f(U) | OR | Region start-end | Genes |
|---|---|---|---|---|---|---|---|---|---|---|
| BICF2P401973 | 10 | 65344772 | 3.79E-04 | 1 | G | 0.84 | 0.71 | 2.23 | No LD | MITD1, TRNAK-CUU, LIPT1, TSGA10 FAM161A, CCT4, COMMD1, TRNAE-UUC, TMEM17, EHBP1 |
| BICF2P454456 | 11 | 32175491 | 4.77E-04 | 3 | A | 0.19 | 0.13 | 1.62 | 31831896-32175491 | C11H9orf123, PTPRD |
| BICF2P50610 | 11 | 32270617 | 2.75E-05 | 3 | A | 0.29 | 0.19 | 1.70 | 31939564-32270617 | C11H9orf123, PTPRD |
| BICF2P531097 | 11 | 32908558 | 3.58E-04 | 3 | A | 0.44 | 0.29 | 1.92 | 32908558-32922914 | PTPRD |
| BICF2P1290820 | 11 | 32922914 | 4.19E-04 | 3 | G | 0.44 | 0.30 | 1.91 | | |
| BICF2P65003 | 12 | 40691540 | 3.15E-04 | 2 | G | 0.71 | 0.61 | 1.61 | 40691540-41066621 | SENP6, MYO6, IMPG1 |
| BICF2G630606359 | 13 | 13352804 | 4.61E-04 | 2 | G | 0.69 | 0.57 | 1.67 | 13352804-13503950 | NUDCD1, ENY2, PKHD1L1, EBAG9, SYBU |
| BICF2S23620879 | 14 | 10265645 | 4.05E-04 | 3 | C | 0.5 | 0.37 | 1.71 | 9796003-10265645 | COPG2, MEST, CEP41, CPA1, CPA5, CPA4, CPA2, SSMEM1, TMEM209, KLDHC10, TRNAM-CAU, ZC3HC1, UBE2H, NRF1, SMKR1, STRIP2, AHCYL2, SMO, TSPAN33, TNPO3, IRF5, KCP, ATP6V1F, FLNC |
| BICF2G630519882 | 14 | 11686985 | 4.99E-04 | 3 | A | 0.49 | 0.36 | 1.74 | 11675474-11686985 | LRRC4, SND1, PAX4, FSCN3, ARF5, GCC1, ZNF800, GRM8 |
| BICF2P594418 | 15 | 58424953 | 4.48E-04 | 2 | A | 0.19 | 0.10 | 2.07 | No LD | FAM198B, TMEM144, RXFP1, ETFDH, PPID, FNIP2 |
| BICF2G630422966 | 15 | 58852255 | 4.41E-04 | 3 | A | 0.41 | 0.28 | 1.80 | 58852255-58978372 | RAPGEF2, C15H4orf45 |
| BICF2G630422956 | 15 | 58891376 | 4.41E-04 | 3 | A | 0.41 | 0.28 | 1.80 | | |
| BICF2G630422900 | 15 | 58967776 | 2.04E-04 | 3 | G | 0.37 | 0.24 | 1.87 | | |
| BICF2G630422895 | 15 | 58978372 | 1.69E-04 | 3 | A | 0.37 | 0.24 | 1.89 | | |
| BICF2P880005 | 17 | 20749191 | 2.22E-04 | 1, 2 | G | 0.44 | 0.31 | 1.75 | No LD | KLHL29 |
| BICF2P1121006 | 18 | 54279578 | 1.11E-04 | 1, 2, 3 | A | 0.63 | 0.42 | 2.28 | No LD | CCDC87, DPP3, NPAS4, SLC29A2, BRMS1, RIN1, CD248, CNIH2, RAB1B, KLC2, PACS1, GAL3ST3, SART1, TSGA10IP, C18H11orf68, FOSL1, CTSW, CFL1, SNX32, OVOL1, RNASEH2C, KAT5, RELA, SIPA1, PCNXL3, MAP3K11, KCNK7, EHBP1L1, LTBP3, SCYL1 |
| BICF2P888055 | 20 | 13815084 | 3.25E-04 | 3 | A | 0.73 | 0.62 | 1.71 | No LD | None |
| BICF2P582174 | 20 | 14124824 | 3.76E-04 | 3 | C | 0.82 | 0.73 | 1.61 | 14118014-14124824 | None |
| TIGRP2P270462 | 20 | 15036973 | 8.51E-05 | 3 | G | 0.85 | 0.75 | 1.88 | 14838270-15053718 | EDEM1, ARL8B |
| BICF2P716829 | 20 | 15048191 | 9.85E-05 | 3 | G | 0.85 | 0.75 | 1.86 | | |
| BICF2P1462185 | 20 | 15053718 | 4.90E-04 | 3 | A | 0.85 | 0.74 | 1.90 | | |
| BICF2P178583 | 20 | 30190042 | 1.41E-04 | 1, 2 | G | 0.48 | 0.31 | 2.09 | 30039696-30190042 | ADAMTS9, PRICKLE2, PSMD6, ATXN7, THOC7, SNTN, SYNPR |
| BICF2S2328420 | 20 | 51150968 | 2.77E-04 | 3 | G | 0.75 | 0.60 | 1.96 | No LD | OR12C09, OR4B10, ADGRE2, ZNF333, EMR3, CLEC17A, NDUFB7, TECR, |

TABLE 2-continued

Anterior cruciate ligament rupture associated SNPs identified by GWAS in the Labrador Retriever, a dog breed with a high disease prevalence

| SNP | chr | Position | P | LMM | Risk Allele | f(A) | f(U) | OR | Region start-end | Genes |
|---|---|---|---|---|---|---|---|---|---|---|
| | | | | | | | | | | DNAJB1, GIPC1, PTGER1, PKN1, DDX39A, CD97, LPHN1, ASF1B, PRKACA, SAMD1, PALM3, IL27RA, RLN3, RFX1, DCAF15, PODNL1, CC2D1A, C20H19orf57, NANOS3, ZSWIM4, C20H19orf53 |
| BICF2P420488 | 20 | 52326317 | 3.84E-04 | 3 | G | 0.85 | 0.75 | 1.84 | 51873051-52326317 | MRI1, CCDC130, CACNA1A, NACC1, NFIX, DAND5, RAD23A, CALR, SYCE2, KLF1, MAST1, RNASEH2A, PRDX2, HOOK2, BEST2, TNPO2, WDR83, MAN2B1, ZNF791, ZNF709, ACP5, ELOF1 |
| TIGRP2P277002 | 20 | 55563965 | 2.25E-04 | 1, 2 | A | 0.25 | 0.10 | 2.98 | No LD | INSR, ARHGEF18, PEX11G, C20H19orf45, MCOLN1, PNPLA6, CAMSAP3, XAB2, PCP2, STXBP2, RETN, C20H19orf59, FCER2, CLEC4G, CD209, EVI5L, LRRC8E, MAP2K7, SNAPC2, CTXN1, TIMM44, ELAVL1, FBN3, CERS4, CD320, RAB11B, MARCH2, PRAM1, ZNF414, MYO1F |
| BICF2P111342 | 21 | 7150110 | 1.25E-04 | 1, 2 | A | 0.31 | 0.18 | 2.04 | No LD | None |
| BICF2G630658881 | 21 | 7582214 | 1.09E-04 | 1, 2, 3 | G | 0.49 | 0.32 | 2.12 | 7582214-8382709 | JRKL, CCDC82, MAML2, MTMR2, CEP57, FAM76B, SESN3 |
| BICF2G630658668 | 21 | 8205285 | 4.03E-04 | 3 | G | 0.49 | 0.32 | 2.00 | | |
| BICF2G630658620 | 21 | 8382709 | 2.90E-04 | 3 | G | 0.50 | 0.33 | 2.02 | | |
| BICF2G630658768 | 21 | 8033283 | 4.09E-04 | 1, 2 | C | 0.27 | 0.14 | 2.28 | 8033283-8061623 | JRKL, CCDC82, MAML2, MTMR2, CEP57, FAM76B, SESN3 |
| BICF2G630658756 | 21 | 8040746 | 4.73E-04 | 1 | A | 0.26 | 0.13 | 2.30 | | |
| BICF2G630658723 | 21 | 8061623 | 4.09E-04 | 1, 2 | G | 0.27 | 0.14 | 2.28 | | |
| BICF2S2442023 | 21 | 43533585 | 3.19E-04 | 3 | G | 0.50 | 0.34 | 1.93 | 43507320-43533585 | NUCB2, NCR3LG1, KCNJ11, ABCC8, USH1C, OTOG, MYOD1, KCNC1, SERGEF, TPH1, SAAL1, SAA1, HPS5, GTF2H1, LDHA |
| BICF2S2361376 | 21 | 43752575 | 1.76E-04 | 1, 2, 3 | A | 0.60 | 0.42 | 1.97 | 43752575-43808389 | LDHC, TSG101, UEVLD, SPTY2D1, TMEM86A, IGSF22, PTPN5 |
| BICF2P321064 | 21 | 44627903 | 1.66E-04 | 1, 2, 3 | G | 0.38 | 0.24 | 1.99 | No LD | MRGPRX2, ZDHHC13, CSRP3, E2F8, NAV2 |
| TIGRP2P293361 | 22 | 42354230 | 2.27E-04 | 2 | A | 0.49 | 0.36 | 1.74 | No LD | SLITRK5 |
| TIGRP2P297337 | 22 | 58201452 | 1.08E-04 | 1, 2, 3 | A | 0.44 | 0.27 | 2.20 | No LD | EFNB2, ARGLU1 |
| BICF2G630375268 | 23 | 33376383 | 3.48E-04 | 3 | A | 0.74 | 0.63 | 1.75 | No LD | TEMEM108, BFSP2, CDV3, TOPBP1, TF, SRPRB, RAB6B, C23H3orf36, SLCO2A1 |

TABLE 2-continued

Anterior cruciate ligament rupture associated SNPs identified by GWAS in the Labrador Retriever, a dog breed with a high disease prevalence

| SNP | chr | Position | P | LMM | Risk Allele | f(A) | f(U) | OR | Region start-end | Genes |
|---|---|---|---|---|---|---|---|---|---|---|
| BICF2S23730962 | 23 | 53809871 | 2.93E−04 | 2 | A | 0.87 | 0.78 | 1.88 | No LD | TIPARP, LEKR1, CCNL1, VEPH1, PTX3 |
| BICF2G630502225 | 24 | 23992936 | 4.86E−04 | 2 | G | 0.92 | 0.81 | 2.84 | | |
| BICF2G630500368 | 24 | 30241088 | 2.76E−07 | 1, 2, 3 | G | 0.83 | 0.66 | 2.56 | 30241088-30245795 | BPI LBP, RALGAPB, ADIG, ARHGAP40, SLC32A1, ACTR5, PPP1R16B, FAM83D, DHX35 |
| BICF2G630500363 | 24 | 30245795 | 1.82E−06 | 1, 2, 3 | G | 0.80 | 0.62 | 2.44 | | |
| BICF2G630500835 | 24 | 29648925 | 1.29E−04 | 2, 3 | A | 0.79 | 0.67 | 1.90 | No LD | CTNNBL1, VSTM2L, TTI1, RPRD1B, TGM2, KIAA1755 |
| BICF2P544126 | 24 | 29772193 | 4.09E−05 | 3 | G | 0.94 | 0.87 | 2.28 | 29772193-29794411 | BPI LBP, RALGAPB, ADIG, ARHGAP40, SLC32A1, ACTR5, PPP1R16B, FAM83D, DHX35, CTNNBL1, VSTM2L, TTI1, RPRD1B, TGM2, KIAA1755 |
| BICF2S24111418 | 24 | 29794411 | 4.09E−05 | 3 | A | 0.94 | 0.87 | 2.28 | | |
| BICF2G630799191 | 26 | 22848912 | 1.33E−04 | 3 | G | 0.61 | 0.45 | 1.92 | No LD | ADRBK2, MYO18B, SEZ6L, ASPHD2, HPS4, SRRD, TFIP11, TPST2, CRYBB1, CRYBA4 |
| BICF2P792911 | 26 | 22894961 | 8.55E−05 | 1, 2, 3 | G | 0.44 | 0.27 | 2.14 | No LD | ADRBK2, MYO18B, SEZ6L, ASPHD2, HPS4, SRRD, TFIP11, TPST2, CRYBB1, CRYBA4 |
| BICF2S2356299 | 27 | 30557856 | 2.21E−05 | 2, 3 | A | 0.43 | 0.27 | 2.03 | No LD | AEBP2, PLEKHA5 |
| BICF2P1332722 | 27 | 30603252 | 2.19E−04 | 1, 2 | G | 0.78 | 0.60 | 2.33 | No LD | AEBP2, PLEKHA5 |
| BICF2P1047447 | 27 | 31108106 | 2.80E−04 | 3 | A | 0.52 | 0.38 | 1.75 | No LD | CAPZA3, PLCZ1, PIK3C2G |
| BICF2P487060 | 27 | 33778510 | 4.55E−04 | 3 | C | 0.40 | 0.27 | 1.81 | 33778510-33809600 | MGST1, SLC15A5, DERA, STRAP, EPS8, PTPRO |
| BICF2P599881 | 27 | 35600038 | 2.66E−04 | 3 | G | 0.85 | 0.74 | 1.97 | No LD | PLBD1, ATF7IP, GRIN2B |
| BICF2P1410038 | 27 | 37697040 | 3.33E−04 | 3 | C | 0.70 | 0.56 | 1.82 | No LD | BCL2L14, ETV6, TAS2R42, CAFA-T2R67, CAFA-T2R43, CAFA-T2R12, TAS2R10, TAS2R9, TAS2R8, TAS2R7, CSDA, STYK1, MAGOHB, KLRA1 |
| BICF2S23535135 | 27 | 37814333 | 1.13E−04 | 3 | A | 0.31 | 0.20 | 1.83 | No LD | BCL2L14, ETV6, TAS2R42, CAFA-T2R67, CAFA-T2R43, CAFA-T2R12, TAS2R10, TAS2R9, TAS2R8, TAS2R7, CSDA, STYK1, MAGOHB, KLRA1 |
| TIGRP2P355298 | 27 | 39134291 | 1.31E−04 | 3 | G | 0.74 | 0.57 | 2.16 | No LD | KLRK1, KLRD1, GABARAPL1, TMEM52B, OLR1, CLEC7A, CLEC1A, CLEC9A, CLEC12A, KLRF2, CD69, CLEC2D, KLRB1, PZP |
| BICF2S23255928 | 27 | 39211186 | 1.10E−04 | 2, 3 | A | 0.23 | 0.13 | 2.07 | 39211186-39217437 | A2M |
| BICF2P526639 | 27 | 39217437 | 4.12E−05 | 2, 3 | G | 0.23 | 0.12 | 2.18 | | |
| BICF2S23152419 | 27 | 39428263 | 1.77E−05 | 3 | A | 0.79 | 0.64 | 2.13 | 39428263-39445306 | KLRG1, M6PR, PHC1, A2ML1 |
| BICF2P491441 | 27 | 39434491 | 3.34E−04 | 3 | G | 0.78 | 0.63 | 2.06 | | |
| TIGRP2P355396 | 27 | 39445306 | 3.34E−04 | 3 | A | 0.78 | 0.63 | 2.06 | | |

TABLE 2-continued

Anterior cruciate ligament rupture associated SNPs identified by GWAS in the Labrador Retriever, a dog breed with a high disease prevalence

| SNP | chr | Position | P | LMM | Risk Allele | f(A) | f(U) | OR | Region start-end | Genes |
|---|---|---|---|---|---|---|---|---|---|---|
| BICF2P337576 | 27 | 39463031 | 2.35E-04 | 3 | G | 0.70 | 0.55 | 1.92 | 39346073-39511019 | RMKLB |
| BICF2P794117 | 27 | 39511019 | 3.76E-04 | 3 | C | 0.71 | 0.56 | 2.00 | | |
| BICF2P155064 | 27 | 39526004 | 4.68E-04 | 3 | G | 0.21 | 0.14 | 4.78 | No LD | None |
| BICF2P992747 | 27 | 39580957 | 1.65E-04 | 3 | A | 0.77 | 0.62 | 2.07 | No LD | MFAP5 |
| BICF2S23652189 | 27 | 39644847 | 3.99E-04 | 3 | G | 0.31 | 0.21 | 1.64 | 39606871-39644847 | AICDA, APOBEC1, DPPA3 |
| TIGRP2P362234 | 28 | 41376035 | 3.71E-04 | 2 | G | 0.87 | 0.74 | 2.37 | 41376035-41377128 | MGMT, EBF, GLRX3 |
| BICF2S23346408 | 28 | 41377128 | 1.25E-04 | 1, 2 | A | 0.87 | 0.73 | 2.53 | | |
| BICF2S23713161 | 29 | 20562935 | 4.59E-04 | 2 | G | 0.75 | 0.63 | 1.74 | No LD | CPA6, PREX2, C29H8orf34 |
| BICF2S23410873 | 29 | 20672864 | 2.18E-04 | 2, 3 | C | 0.82 | 0.66 | 2.35 | 20672864-20703202 | CPA6, PREX2, C29H8orf34 |
| BICF2P1135545 | 29 | 20703202 | 2.81E-04 | 2, 3 | A | 0.82 | 0.67 | 2.31 | | |
| BICF2P483191 | 29 | 21601273 | 2.31E-05 | 1, 2, 3 | C | 0.73 | 0.51 | 2.54 | No LD | SULF1, SLCO5A1, PRDM14, NCOA2, TRAM1 |
| BICF2P139173 | 29 | 22067666 | 3.59E-04 | 2 | A | 0.50 | 0.36 | 1.79 | 22050835-22191229 | SULF1, SLCO5A1, PRDM14, NCOA2, TRAM1 |
| BICF2P361907 | 29 | 22191229 | 3.47E-04 | 2 | G | 0.50 | 0.36 | 1.75 | | |
| BICF2P456086 | 29 | 23130206 | 4.85E-04 | 3 | A | 0.88 | 0.71 | 3.04 | No LD | XKR9, EYA1 |
| BICF2P662502 | 29 | 26040013 | 3.24E-04 | 1, 2 | G | 0.90 | 0.73 | 2.87 | No LD | JPH1, GDAP1, PI15, CRISPLD1 |
| BICF2G630412697 | 30 | 3126573 | 7.22E-05 | 1, 3 | G | 0.96 | 0.86 | 4.23 | No LD | COR4F22P, COR4F25, COR4F24P, COR4T2P |
| BICF2S2356993 | 31 | 12920807 | 2.25E-04 | 2, 3 | A | 0.25 | 0.14 | 2.04 | No LD | None |
| BICF2P287265 | 31 | 30555902 | 4.38E-04 | 3 | G | 0.96 | 0.87 | 3.38 | No LD | MIS18A, MRAP, URB1, EVA1C, C31H21orf59, SYNJ1, PAXBP1, C31H21orf62, OLIG2, OLIG1, DONSON, ATP5O, IFNAR2, IL10RB |
| BICF2S23054250 | 35 | 26868731 | 2.20E-04 | 2, 3 | A | 0.49 | 0.33 | 1.97 | No LD | LRRC16A, SCGN, HIST1H2AA, HIST1H2BA, SLC17A4, SLC17A1, TRIM38, HFE, HIST1H1T, BTN2A2, BTN1A1 |
| BICF2P1086740 | 37 | 26916351 | 4.34E-04 | 2 | G | 0.41 | 0.24 | 2.18 | No LD | SMARCAL1, RPL37A, IGFBP2, IGFBP5, TNP1 |
| BICF2P708698 | 37 | 26924473 | 1.53E-04 | 2 | A | 0.63 | 0.45 | 2.06 | No LD | SMARCAL1, RPL37A, IGFBP2, IGFBP5, TNP1 |

Note:
OR odds ratio calculated from PLINK. LMM Linear mixed model 1 - GCTA, 2 - GEMMA, 3 - PUMA.
SNP position and genomic regions are based on CanFam 2.0.

TABLE 3

Statistical Power and odds ratio correction for anterior cruciate ligament rupture GWAS risk loci identified by GEMMA in the Labrador Retriever

| SNP | CFA | MAF | Beta | Significance | OR | f(u) | Power | Corrected OR | Corrected Power | INPower Estimated number of loci |
|---|---|---|---|---|---|---|---|---|---|---|
| BICF2S23638642 | 1 | 0.116 | 0.2327823 | 4.95E-04 | 3.07 | 0.07 | 0.986 | 1.38 | 0.188 | 6.1 |
| BICF2S22959529 | 1 | 0.07595 | 0.3139731 | 1.58E-04 | 4.78 | 0.03 | 0.991 | 1.83 | 0.304 | 3.9 |
| BICF2P247448 | 2 | 0.3957 | -0.1791686 | 1.48E-04 | 1.67 | 0.55 | 0.835 | 1.23 | 0.224 | 2.6 |
| BICF2G630464857 | 2 | 0.08439 | 0.3041543 | 2.00E-04 | 3.69 | 0.04 | 0.976 | 1.58 | 0.229 | 3.7 |
| BICF2P564273 | 3 | 0.4072 | -0.173683 | 1.07E-04 | 2.16 | 0.52 | 0.993 | 1.47 | 0.611 | 3.5 |
| BICF2G630349775 | 3 | 0.1181 | 0.2355141 | 4.26E-04 | 2.9 | 0.07 | 0.975 | 1.37 | 0.181 | 5.5 |
| BICF2S24415473 | 3 | 0.3165 | 0.1940324 | 7.07E-05 | 1.97 | 0.26 | 0.963 | 1.5 | 0.594 | 2.0 |
| BICF2G630359517 | 3 | 0.4198 | 0.1503946 | 3.77E-04 | 1.82 | 0.36 | 0.937 | 1.2 | 0.182 | 6.2 |
| BICF2G63058646 | 4 | 0.07806 | 0.3008072 | 1.76E-04 | 3.71 | 0.04 | 0.977 | 1.62 | 0.251 | 4.1 |
| BICF2P295392 | 4 | 0.06962 | 0.2949176 | 4.61E-04 | 3.07 | 0.04 | 0.908 | 1.39 | 0.138 | 5.9 |

TABLE 3-continued

Statistical Power and odds ratio correction for anterior cruciate ligament rupture GWAS risk loci identified by GEMMA in the Labrador Retriever

| SNP | CFA | MAF | Beta | Significance | OR | f(u) | Power | Corrected OR | Corrected Power | INPower Estimated number of loci |
|---|---|---|---|---|---|---|---|---|---|---|
| BICF2G630175389 | 4 | 0.2616 | −0.2019631 | 5.87E−05 | 2.28 | 0.68 | 0.984 | 1.69 | 0.773 | 2.3 |
| BICF2P498515 | 6 | 0.09958 | 0.2861419 | 7.89E−05 | 3.11 | 0.06 | 0.978 | 1.93 | 0.573 | 3.4 |
| BICF2P1072682 | 7 | 0.1957 | 0.2030288 | 4.09E−04 | 2.42 | 0.14 | 0.986 | 1.3 | 0.208 | 4.1 |
| BICF2P1208798 | 9 | 0.4388 | 0.2050435 | 5.49E−05 | 2.27 | 0.36 | 0.998 | 1.7 | 0.87 | 1.9 |
| BICF2P890246 | 9 | 0.2764 | −0.2119253 | 3.23E−05 | 2.99 | 0.36 | 1 | 2.19 | 0.996 | 2.5 |
| BICF2P65003 | 12 | 0.3481 | −0.2006769 | 3.15E−04 | 1.61 | 0.61 | 0.75 | 1.16 | 0.134 | 2.5 |
| BICF2G630606359 | 13 | 0.3825 | −0.1598137 | 4.61E−04 | 1.67 | 0.57 | 0.827 | 1.16 | 0.137 | 4.8 |
| BICF2P594418 | 15 | 0.1414 | 0.2242702 | 4.48E−04 | 2.07 | 0.1 | 0.84 | 1.24 | 0.129 | 4.6 |
| BICF2P880005 | 17 | 0.3671 | 0.1722047 | 2.22E−04 | 1.75 | 0.31 | 0.89 | 1.21 | 0.186 | 4.0 |
| BICF2P1121006 | 18 | 0.4916 | −0.209966 | 1.11E−04 | 2.28 | 0.42 | 0.998 | 1.5 | 0.663 | 1.6 |
| BICF2P178583 | 20 | 0.3776 | 0.176725 | 1.41E−04 | 2.09 | 0.31 | 0.989 | 1.36 | 0.408 | 3.4 |
| TIGRP2P277002 | 20 | 0.1624 | 0.2345241 | 2.25E−04 | 2.98 | 0.1 | 0.996 | 1.45 | 0.301 | 3.0 |
| BICF2P111342 | 21 | 0.05907 | 0.2031308 | 1.25E−04 | 2.04 | 0.18 | 0.946 | 1.38 | 0.34 | 3.1 |
| BICF2G630658881 | 21 | 0.3903 | 0.1872034 | 1.09E−04 | 2.12 | 0.32 | 0.991 | 1.45 | 0.559 | 2.0 |
| BICF2G630658768 | 21 | 0.1899 | 0.2129482 | 4.09E−04 | 2.28 | 0.14 | 0.97 | 1.28 | 0.189 | 3.9 |
| BICF2S2361376 | 21 | 0.4873 | 0.1678988 | 1.76E−04 | 1.97 | 0.42 | 0.979 | 1.28 | 0.304 | 3.8 |
| BICF2P321064 | 21 | 0.2975 | 0.1845238 | 1.66E−04 | 1.99 | 0.24 | 0.962 | 1.29 | 0.266 | 3.7 |
| TIGRP2P293361 | 22 | 0.4156 | 0.1686531 | 2.27E−04 | 1.74 | 0.36 | 0.897 | 1.21 | 0.195 | 4.0 |
| TIGRP2P297337 | 22 | 0.3397 | 0.1873248 | 1.08E−04 | 2.2 | 0.27 | 0.993 | 1.48 | 0.573 | 2.3 |
| BICF2S23730962 | 23 | 0.1857 | −0.2162607 | 2.93E−04 | 1.88 | 0.78 | 0.789 | 1.22 | 0.152 | 3.8 |
| BICF2G630502225 | 24 | 0.1435 | −0.223976 | 4.86E−04 | 2.84 | 0.81 | 0.978 | 1.35 | 0.254 | 4.4 |
| BICF2G630500835 | 24 | 0.2827 | −0.1744313 | 1.29E−04 | 1.9 | 0.67 | 0.912 | 1.33 | 0.332 | 4.4 |
| BICF2G630500368 | 24 | 0.27 | −0.2641268 | 2.76E−07 | 2.56 | 0.66 | 0.997 | 2.44 | 0.995 | 0.8 |
| BICF2P792911 | 26 | 0.3432 | 0.1878882 | 8.55E−05 | 2.14 | 0.27 | 0.989 | 1.53 | 0.645 | 2.2 |
| BICF2S2356299 | 27 | 0.339 | 0.1673825 | 2.21E−05 | 2.03 | 0.27 | 0.977 | 1.71 | 0.842 | 4.2 |
| BICF2P1332722 | 27 | 0.3228 | −0.1794126 | 2.19E−04 | 2.33 | 0.6 | 0.996 | 1.34 | 0.378 | 3.8 |
| BICF2P526639 | 27 | 0.1695 | 0.2271469 | 4.12E−05 | 2.18 | 0.12 | 0.927 | 1.71 | 0.626 | 3.5 |
| BICF2S23346408 | 28 | 0.211 | −0.2180301 | 1.25E−04 | 2.53 | 0.73 | 0.989 | 1.53 | 0.55 | 2.2 |
| BICF2S23713161 | 29 | 0.3186 | −0.1592704 | 4.59E−04 | 1.74 | 0.63 | 0.85 | 1.18 | 0.152 | 6.2 |
| BICF2S23410873 | 29 | 0.2722 | −0.17516 | 2.18E−04 | 2.35 | 0.66 | 0.992 | 1.34 | 0.351 | 4.6 |
| BICF2P483191 | 29 | 0.3948 | −0.2013067 | 2.31E−05 | 2.54 | 0.51 | 1 | 2.02 | 0.982 | 2.3 |
| BICF2P361907 | 29 | 0.4198 | 0.1766305 | 3.47E−04 | 1.75 | 0.36 | 0.903 | 1.19 | 0.17 | 2.8 |
| BICF2P662502 | 29 | 0.2025 | −0.1924562 | 3.24E−04 | 2.87 | 0.73 | 0.997 | 1.39 | 0.372 | 4.9 |
| BICF2S2356993 | 31 | 0.1857 | 0.2003128 | 2.25E−04 | 2.04 | 0.14 | 0.907 | 1.27 | 0.18 | 4.7 |
| BICF2S23054250 | 35 | 0.3945 | 0.1628769 | 2.20E−04 | 1.97 | 0.33 | 0.975 | 1.26 | 0.258 | 4.1 |
| BICF2P1086740 | 37 | 0.3143 | 0.1743002 | 4.34E−04 | 2.18 | 0.24 | 0.989 | 1.26 | 0.227 | 4.1 |
| BICF2P708698 | 37 | 0.4768 | −0.1611546 | 1.53E−04 | 2.06 | 0.45 | 0.989 | 1.33 | 0.389 | 4.1 |

Note:
OR odds ratio calculated from PLINK. Corrected OR was calculated using an approximate conditional likelihood approach [Ghosh A, Zou F, Wright FA. Estimating odds ratios in genome scans: An approximate conditional likelihood approach. Am J Human Genet. 2008; 82: 1064-1074]. GWAS data were derived using GEMMA. For each risk locus detected by GEMMA, the total number of risk loci was estimated using INPower [Park J-HM, Wacholder S, Gail M, Peters U, Jacobs KB, Chanock SJ, et al. Estimation of effect size distribution from genome-wide association studies and implications for future discoveries. Nat Genet. 2010; 42: 570-575].

Figure 3:
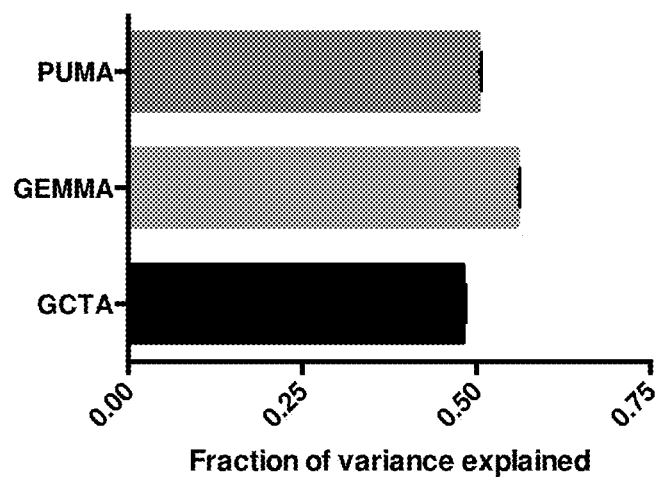
FIG. 3 is a graph showing that phenotype variance was explained to a large degree by the associate genomic loci. Loci identified by linear mixed model (LMM) analysis were broadly defined as SNPs with $r^2>0.5$ within 5 Mb of the peak SNP. For GCTA, 36 loci in 72.7 Mb of the genome explained 48.09% of the phenotypic variance. For GEMMA, 47 loci in 82.7 Mb of the genome explained 55.88% of the phenotypic variance. For PUMA, 65 loci in 86.58 Mb of the genome explained 50.28% of the phenotypic variance in the ACL rupture trait.

With the Labrador Retriever breed, associated regions (P<5.0E-04) explained the approximately half of the phenotypic variance in the ACL rupture trait (FIG. 3). For GCTA, 36 loci in 72.7 Mb of the genome explained 48.09% of the phenotypic variance. For GEMMA, 47 loci in 82.7 Mb of the genome explained 55.88% of the phenotypic variance. For PUMA, 65 loci in 86.58 Mb of the genome explained 50.28% of the phenotypic variance in the ACL rupture trait.

We identified 129 SNPs associated with canine ACL rupture. By using LD clumping, we found that these SNPs reside in 98 loci. Five of these regions were located in uncharacterized or non-coding regions of the genome. A SNP on CFA24 met genome-wide significance for LMM association analysis with GEMMA and PUMA, but not GCTA (P=3.63E-06). This SNP resides in a 5 kB haplotype block with two other SNPs. Ten genes are located within the locus defined by 500 kB flanking regions including bactericidal/permeability-increased protein (BPI), lipopolysaccharide binding protein (LBP), Ral GTPase activation protein beta subunit (RALGAPB), adipogenin (ADIG), rho GTPase activating protein 40 (ARHGAP40), solute carrier family 32, member 1 (SLC32A1), ARP5 actin-related protein 5 (ACTR5), protein phosphatase 1, regulatory subunit 16B (PPP1R16B), family with sequence similarity 83, member D (FAM83D), and DEAH (Asp-Glu-Ala-His; SEQ. ID. NO: 1) box polypeptide 35(DHX35). Although many risk loci contained large numbers of genes, five loci did not (Table 1, Table 2), suggesting these SNPs may have a regulatory function on gene expression (rSNPs).

Power analysis of our GWAS data set using INPower estimates that 172 loci explain the genetic contribution to ACL rupture in the Labrador Retriever. See Table 3.

Figure 4:
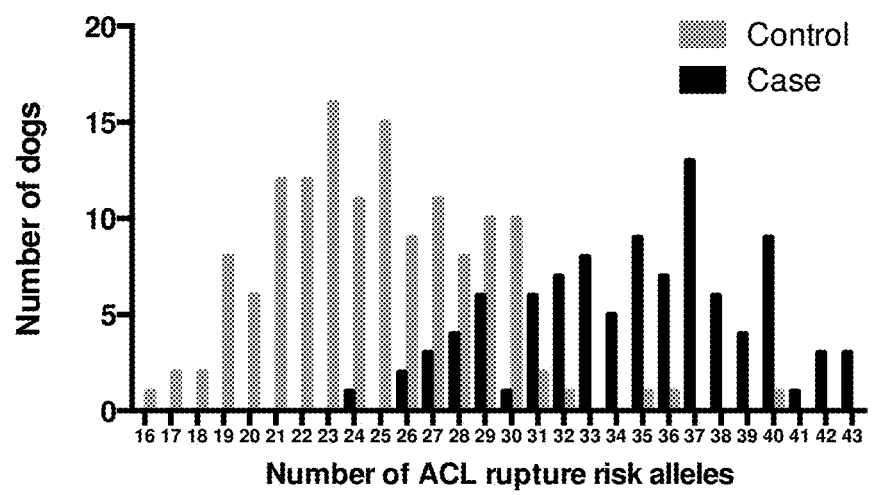
FIG. 4 and FIG. 5 show that genetic risk scoring using GWAS associated loci from linear mixed model analysis with GEMMA predicts ACL rupture disease risk in both case and control Labrador Retriever dogs.
Figure 5:
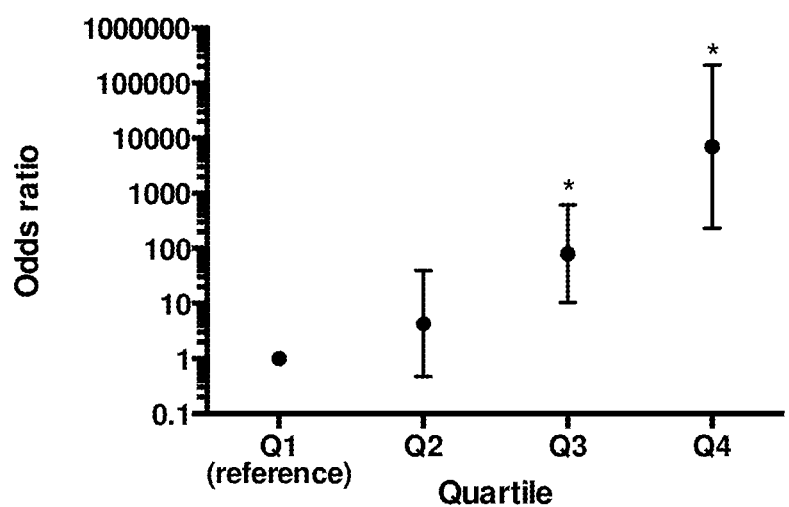

Risk Loci Clearly Distinguish ACL Rupture Cases from Controls:

To evaluate the cumulative effects of associated ACL rupture risk loci, we used a genetic risk scoring approach using a simple allele count (cGRS) or a weighted approach (wGRS). We found significant differences in the number of risk alleles in cases and controls for GCTA (P<2.2E-16), GEMMA (P<2.2E-16), and PUMA (P<2.2E-16) (Table 4), with a shift to increased numbers of risk alleles in the cases. See FIGS. 4 and 5. When the odds ratios according to the wGRS quartiles for each LMM were calculated, there was a significant increase in ACL rupture odds ratios with increasing wGRS quartile for all three LMM, using the first wGRS quartile as a reference (FIGS. 4 and 5)

TABLE 4

Genetic risk scoring in anterior cruciate ligament rupture case and control Labrador Retriever dogs using GWAS associated SNPs from linear mixed model analysis

| | Number of Risk alleles | | |
|---|---|---|---|
| LMM | Control | Case | Significance |
| GCTA | 24 (16, 40) | 35 (24, 43) | P < 2.2E−16 |
| GEMMA | 33 (22, 43) | 45 (29, 55) | P < 2.2E−16 |
| PUMA | 62 (37, 84) | 77 (56, 99) | P < 2.2E−16 |

Note:
Data represent median (range) for allele counting (cGRS). LMM Linear mixed models used were GCTA, GEMMA, PUMA. The Mann-Whitney U test was used to determine significance.

AUC differences between cGRS and wGRS were small and we found that there were no significant differences in ROC AUC for cGRS and wGRS for any of the three LMM analyses. For both cGRS and wGRS analyses, GCTA and GEMMA yielded increased ROC AUC values, when compared with PUMA. Overall, cGRS for GEMMA yielded the highest AUC at 0.9634 (Table 5).

TABLE 5

Receiver operating characteristic (ROC) analysis of genetic risk scoring in anterior cruciate ligament rupture case and control Labrador Retriever dogs using GWAS associated SNPs from linear mixed model analysis

| | Area under the ROC curve | | Significance | |
|---|---|---|---|---|
| LMM | cGRS | 95% confidence interval | wGRS | 95% confidence interval |
| GCTA | 0.9487 | 0.9191-0.9725 | 0.9464 | 0.9183-0.9694 |
| GEMMA | 0.9634 | 0.9369-0.9824 | 0.9601 | 0.933-0.9801 |
| PUMA | 0.8842* | 0.8356-0.9158 | 0.8909* | 0.8458-0.9263 |

Note:
LMM Linear mixed models used were GCTA, GEMMA, PUMA.
*Significantly different from GCTA and GEMMA (P < 0.005 for cGRS and P < 0.05 for wGRS).

GWAS Pathways are Enriched for Aggrecan Signaling:

Functional annotation clustering using DAVID revealed association with a cluster of four genes (CD209, ACAN, KLRA1, KLRD1) (P<2.3E-03, $P_{corr}$=0.059) that includes aggrecan (ACAN), a large structural protein that stabilizes the collagen network in ligament matrix [30]. Using INRICH, we identified enrichment for a single set of genes (TTR, SLC9A5, SLC10A1, SLC37A4, SLC6A1, AQP9. GABRP, GJB1, KCNJ3, ALB, GABRB3, P2RX1, SLC16A2) (P<4.0E-4, $P_{corr}$=0.07). This pathway primarily consists of genes encoding membrane transport proteins with a wide range of physiological functions including pH regulation, glucose homeostasis, signal transduction.

ACL Rupture in the Labrador Retriever has Moderate Heritability:

Using a Bayesian method, narrow sense genetic heritability of ACL rupture was estimated at 0.538. Broad sense heritability from pedigrees was estimated at 0.521. After correction to the liability scale for a binary trait, these estimates were 0.493 and 0.476, respectively.

Discussion:

By undertaking a within-breed GWAS in the Labrador Retriever, we found 98 regions of association with the trait, suggesting that ACL rupture is a complex, potentially highly polygenic condition. These loci explained between 48% and 56% of the disease risk phenotype, depending on which LMM was used for the association analysis, suggesting that inherited factors make an important contribution to the disease. We estimated narrow sense genetic heritability to be 0.49 and broad sense heritability to be 0.48, higher values than past estimates in the Newfoundland and Boxer breeds. Wilke V L, Conzemius M G, Kinghorn B P, Macrossan P E, Cai W, Rothschild M F. Inheritance of rupture of cranial cruciate ligament in Newfoundlands. J Am Vet Med Assoc. 2006;228: 61-64. Nielen A L, Janss L L, Knol B W. Heritability estimations for diseases, coat color, body weight, and heigh in a birth cohort of Boxers. Am J Vet Res. 2001;62: 1198-1206.

Our study population of Labrador Retriever dogs was typical of the general population, with an approximately equal numbers of male and female dogs and a large majority of the dogs being neutered by castration or ovariohysterectomy, respectively. ACL rupture in dogs is an acquired condition. In the present study, ACL rupture cases were middle-aged dogs typically, with a mean age of 6.0 years. In dogs, loss of sex steroids through neutering is a risk factor for ACL rupture [Whitehair J G, Vasseur P B, Willits N H. Epidemiology of cranial cruciate ligament rupture in dogs. J Am Vet Med Assoc. 1993;203: 1016-1019]. In human beings, ACL rupture is predisposed to female athletes [Sutton K M, Bullock J M. Anterior cruciate ligament rupture: Differences between males and females. J Am Acad Orthop Surg. 2013;21: 41-50]. Knee laxity in women is lowest in the follicular phase of the menstrual cycle (low estrogen), when ACL rupture is most common. Beynnon B D, Johnson R J, Braun S, Sargent M, Bernstein I M, et al. The relationship between menstrual cycle phase and anterior cruciate ligament injury. Am J Sports Med. 2006;34: 757-764. Hewett T E, Zazulak B T, Myer G D. Effects of the menstrual cycle on anterior cruciate ligament injury risk. Am J Sports Med. 2007;35: 659-668. [33,34]. This suggests that the influence of sex steroid levels on ACL laxity in both species may influence accumulation of matrix damage over time and consequently risk of rupture.

Because of the high LD within breeds of dogs, risk loci often contained large numbers of genes. However, several risk loci appeared to contain rSNPs located in gene deserts in intergenic regions of the genome of >500 kb that lack annotated genes or protein-coding sequences. Schierding W, Cutfield W S, O'Sullivan J M. The missing story behind genome wide association studies: single nucleotide polymorphisms in gene deserts have a story to tell. Front Genet. 2014;5: 39. Complex trait disease is caused by disturbance to biological networks, not isolated genes or proteins. Regulatory SNPs can influence gene expression through a number of mechanisms that include the three dimensional organization of the genome, RNA splicing, transcription factor binding, DNA methylation, and long non-coding RNAs (lncRNA). Huang Q. Genetic study of complex diseases in the post-GWAS era. J Genet Genomics. 2015;42: 87-98. Investigation of SNPs associated with complex trait disease in dogs with potential regulatory function through expressed quantitative trait loci (eQTL) studies or other methods is currently lacking.

One locus consisting of a 5 kb haplotype block with two other SNPs on CFA 24 met genome-wide significance in the present study. Ten genes were identified in this block with diverse physiological effects on cellular and tissue homeostasis. For example, ACTR5 plays an important role in chromatin remodeling during transcription, DNA repair, and DNA regulation. DHX35 encodes an ATP-ase that plays a role in RNA splicing [40] and RALBAPB as well as FAM83D are both important for mitotic regulation. While a relationship between cellular homeostasis/proliferation and ACL rupture has not been established, it is feasible that aberrations in the genes that govern these processes could have a wide range of effects that may alter ligament tissue integrity. Other genes in this block include LBP and BPI, which have in important function regarding immuno-stimulatory capacity of innate immune mechanisms. Certain LBP genotypes have been associated with chronic inflammatory disease [Schumann R. Old and new findings on lipopolysaccharide-binding protein: a soluble pattern-recognition molecule. Biochem Soc Trans. 2011:39: 989-993]. Notably, PPP1R16B encodes a protein that promotes angiogenesis through inhibition of Phosphatase and tensin homolog (PTEN) [Obeidat M, Li L, Ballermann B. TIMAP promotes angiogenesis by suppressing PTEN-mediated Akt inhibition in human glomerular endothelial cells. Am J Physiol Renal Physiol. 2014:307: F623-F633]. The angiogenesis-associated signaling cascade is important for ligament matrix remodeling following mechanical loading, and variations in this cascade have been associated with non-contact ACL rupture risk [Rahim M, Gibbon A, Hobbs H, vander Merwe W, Posthumus M, Collins M, et al. The association of genes involved in the angiogenesis-associated signaling pathway with risk of anterior cruciate ligament rupture. J Orthop Res. 2014;32: 1612-1618].

To further investigate the large number of genes we identified within risk loci, we also undertook pathway analysis of our data using two different methods. Pathway analysis using DAVID revealed an association with a cluster of four carbohydrate-binding protein genes including aggrecan (ACAN). Aggrecan is a large aggregating proteoglycan that, through binding to fixed charged groups, maintains osmotic pressure in collagenous tissues to promote water retention. Tissue hydration is important for efficient distribution of load and for the ability of cells to accomplish repair. Equine degenerative suspensory ligament desmitis (DSLD), a debilitating disorder of horses that leads to collagen disruption and eventual failure of the suspensory ligament, is associated with a 15-fold increase in aggrecan content of affected ligaments [Plaas A, Sandy J D, Liu H, Diaz M A, Schenkman D, Magnus R P, et al. Biochemical identification and immunolocalization of aggrecan, ADAMTS5 and inter-alpha-trypsin-inhibitor in equine degenerative suspensory ligament desmitis. J Orthop Res. 2011;29: 900-906]. Moreover, recent work has linked human ACAN rs1516797 with the risk of ACL injury in both male and female participants [Mannion S, Mtintsilana A, Posthumus M, van der Merve W, Hobbs H, Collins M, et al. Genes encoding proteoglycans are associated with risk of anterior cruciate ligament ruptures. Br J Sports Med. 2014;48: 1640-1646]. A separate study revealed ACAN gene expression is up-regulated in ACL samples from female compared to male patients that have undergone ACL repair surgery, suggesting a possible etiology for the observed sex differences among patients with ACL injury. The precise mechanism by which ACAN up-regulation may lead to ligament weakening is currently unclear, though a structural change appears to be the most likely etiology.

We also tested genomic regions associated with ACL rupture for gene set enrichment using INRICH. One pathway, module 415 from the Molecular Signatures Database, was inflated. This pathway included 13 genes, most of which encode membrane transport proteins with various physiological roles. GJBI is a member of the large connexin family and encodes connexin 32, a gap junction protein that has been implicated in the regulation of collagen synthesis and the matrix remodeling response to mechanical loading of tendon. Young N J, Becker D L, Fleck R A, Goodship A E, Patterson-Kane J C. Maturational alterations in gap junction expression and associated collagen synthesis in response to tendon function. Matrix Biol 2009;28: 311-323. Waggett A D, Benjamin M, Ralphs J R. Connexin 32 and 43 gap junctions differentially modulate tenocyte response to cyclic mechanical load. Eur J Cell Biol. 2006;85: 1145-1154.Other genes in this module are associated with central nervous system function. SLC6A1, GABRP, and GABRB3 are all associated with GABA signaling and mutations in TTR and have been associated with sensorimotor polyneuropathy. Previous work has suggested a role for neurological pathways in susceptibility to ACL rupture in Newfoundland dogs. Baird AEG, Carter S D, Innes J F, Ollier W, Short A. Genome-wide association study identifies genomic regions of association for cruciate ligament rupture in Newfoundland dogs. Animal Genetics. 2014;45: 542-549.

ACL rupture GRSs were calculated for each dog to determine the cumulative effect of ACL rupture-associated loci on disease risk. While previous work found that wGRS better accounted for genetic risk [Chen H, Poon A, Yeung C, Helms C, Pons J, Bowcock A M, et al. A genetic risk score combining ten psoriasis risk loci improves disease prediction. PLoS One. 2011;6: e19454], our study found no difference between cGRS and wGRS for any of the LMMs used. This is consistent with the idea that the ACL rupture phenotype is associated with a large number of genetic loci with small effects. In diseases with genetic loci with large effects, wGRS would more accurately represent the cumulative effect of individual loci on genetic risk. Overall, predictive capability of GRS is high, with a cGRS for GEMMA AUC of approximately 96%, indicating that we have clearly captured genetic loci that contribute to ACL rupture risk in our LMM association analysis. Future work should include verification of predictive capability by applying these methods to a new test cohort of case and control dogs.

Narrow and broad sense heritability of ACL rupture was estimated at 0.49 and 0.46 respectively using a Bayesian method. These estimates are considerably higher than restricted maximum likelihood (REML) heritability estimates that have been calculated for other breeds of dog. It is unclear whether ACL rupture is truly more heritable in the Labrador Retriever compared to other breeds or if the higher value is a reflection of the Bayesian method used. REML estimation of heritability was attempted but was not successful, probably because of the size of the data set.

Best Linear Unbiased Prediction:

A regression analysis was performed on the n=174 dog data set using GCTA-brand Software. The GCTA software is available online at http://www.complextraitgenomics.com/software/gcta/. See also Yang J, Lee S H, Goddard M E and Visscher P M. GCTA: a tool for Genome-wide Complex Trait Analysis. *Am J Hum Genet*. 2011 January 88(1): 76-82. [PubMed ID: 21167468]. Specifically, a restricted maximum likelihood (REML) analysis of the genetic relationship matrix was executed, followed by a genomic best linear unbiased prediction (gBLUP) analysis to arrive at an estimate of total genetic effect (i.e., a breeding value) for each dog. This analysis was then converted to the SNP effects. The 22 SNPs most statistically associated with the phenotype are tabulated in Table 6. The gBLUP coefficients in Table 6 indicate that there are two SNPS that have much larger coefficients than the rest. There are six SNPS with much smaller coefficients, and 14 SNPS with a coefficient of intermediate size. (The positive or negative sign of the coefficients is not relevant; the coefficients are ranked according to their absolute magnitude.)

TABLE 6

BLUP Analysis Results

| snp | chr | ref allele | blup |
|---|---|---|---|
| BICF2S23135243 | 4 | A | 0.000633434 |
| BICF2G630371956 | 23 | A | 0.00058239 |
| BICF2P401973 | 10 | A | −0.000398919 |
| BICF2P526639 | 27 | G | 0.000373218 |
| BICF2S23448539 | 17 | A | −0.000367718 |
| BICF2G630114782 | 16 | A | −0.00036446 |
| BICF2P890246 | 9 | A | −0.000358272 |
| BICF2P170661 | 6 | A | 0.00034582 |
| BICF2G630815470 | 16 | G | −0.000335841 |
| BICF2G630815474 | 16 | A | −0.000335841 |
| TIGRP2P78405_rs9180048 | 6 | A | 0.000317864 |
| BICF2S2356299 | 27 | A | 0.000316762 |
| BICF2P1121006 | 18 | G | −0.000308138 |
| BICF2P260555 | 27 | A | 0.000275776 |
| BICF2P1465216 | 35 | A | 0.000272433 |
| BICF2P599385 | 35 | A | 0.000254262 |
| BICF2P154295 | 5 | C | 0.00021946 |
| BICF2S23645462 | 18 | A | 0.000202448 |
| BICF2P471347 | 27 | A | 0.000197961 |
| BICF2G630373050 | 23 | A | 0.000147584 |
| BICF2P1126668 | 4 | C | −0.000183486 |
| BICF2P412007 | 6 | A | 2.50967E−05 |

Kits:

Kits are provided which contain reagents useful for determining the presence or absence of polymorphisms appearing in the loci and/or genes recited in Table 1. The kits are used with the methods described herein to determine a dog's propensity to develop CCLR.

The kits typically include written instructions. The instructions may optionally provide calibration curves or charts for comparison with the experimentally measured values. The kit generally includes oligonucleotide probes and/or primers that bind specifically with the canine loci identified in Table 1 and thus function to reveal the presence (or absence) of the corresponding SNP. An appropriate amount of the oligonucleotide primers is provided in one or more containers. The primers may also be provided in the form of a "gene chip" or addressed array, such as (for example) those described in U.S. Pat. No. 7,510,841. In such an array, the primers or probes are immobilized on a solid substrate, typically in pre-determined, known locations. The oligonucleotide primers may also be provided suspended in an aqueous solution or as a freeze-dried or lyophilized powder. The container(s) in which the oligonucleotide(s) are supplied can be any conventional container that is capable of holding the supplied form, for instance, hermetically sealed pouches, microfuge tubes, ampoules, or bottles. In some applications, pairs of primers may be provided in pre-measured single use amounts in individual, typically disposable, tubes or equivalent containers. With such an arrangement, the sample to be tested for the presence of SNPs can be added to the individual tubes and amplification carried out directly.

The amount of each oligonucleotide primer supplied in the kit can be any appropriate amount, depending for instance on the market to which the product is directed. For instance, if the kit is adapted for research or clinical use, the amount of each oligonucleotide primer provided would likely be an amount sufficient to prime several PCR amplification reactions. Those of ordinary skill in the art know the amount of oligonucleotide primer that is appropriate for use in a single amplification reaction.

In some embodiments, kits may optionally also include the reagents necessary to carry out nucleotide amplification reactions, including, for instance, DNA sample preparation reagents, appropriate buffers (e.g., polymerase buffer), salts (e.g., magnesium chloride), and deoxyribonucleotides (dNTPs).

Kits may in addition include either labeled or unlabeled oligonucleotide probes for use in detection of SNPs. In certain embodiments, these probes will be specific for a potential polymorphic site that may be present in the target amplified sequences. The appropriate sequences for such a probe will be any sequence that includes one or more of the identified polymorphic sites, particularly those nucleotide positions indicated in Table 1, such that the sequence the probe is complementary to is a polymorphic site. As a general rule, the probes are at least 6 nucleotides in length and typically shorter than roughly 50 nucleotides. The polymorphic site may occur at any position within the length of the probe. It is often beneficial to use longer probes, in order to ensure specificity. Thus, in some embodiments, the probe is at least 8, at least 10, at least 12, at least 15, at least 20, or at least 30 nucleotides.

It may also be advantageous to provide in the kit one or more control sequences for use in the amplification reactions. The design of appropriate positive control sequences is well known to one of ordinary skill in the appropriate art. By way of example, control sequences may comprise canine nucleic acid molecule(s) with known sequence at or near one or more of the target SNP positions described in Table 1.

The kits may optionally include either labeled or unlabeled oligonucleotide probes for use in detection of the in vitro amplified target sequences. The appropriate sequences for such a probe will be any sequence that falls between the annealing sites of the provided oligonucleotide primers, such that the sequence to which the probe is complementary is amplified during the PCR reaction. In certain embodiments, these probes will be specific for a potential polymorphism that may be present in the target amplified sequences.

It may also be advantageous to provide in the kit one or more control sequences for use in the PCR reactions. The design of appropriate positive control sequences is well known to one of ordinary skill in the appropriate art.

Additional components in specific kits may include instructions for carrying out the assay described herein.

CONCLUSIONS

Ninety-eight (98) candidate loci are identified herein which are associated in a statistically significant manner with heritable non-contact CCLR in the Labrador retriever. Of these, the strongest signal is located on a broad region in chromosome 24. The regions identified in this study are useful to guide breeding decisions.

What is claimed is:

1. A method for breeding a dog, comprising
   a) isolating genomic DNA from a first dog;
   b) assaying the genomic DNA of step (a) for one or more single nucleotide polymorphisms (SNPs) wherein the one or more SNPs comprises BICF2S23652189;
   c) detecting an A allele at BICF2S23652189 in the genomic DNA of step (b); and
   d) breeding the first dog having an "A" allele at BICF2S23652189.

2. The method of claim 1, wherein step (b) comprises assaying the genomic DNA for five or more single nucleotide polymorphisms (SNPs).

3. The method of claim 1, wherein step (b) comprises assaying the genomic DNA for ten or more single nucleotide polymorphisms (SNPs).

4. The method of claim 1, wherein step (b) comprises assaying the genomic DNA for fifteen or more single nucleotide polymorphisms (SNPs).

5. The method of claim 1, wherein step (b) comprises assaying the genomic DNA for twenty or more single nucleotide polymorphisms (SNPs).

6. The method of claim 1, wherein step (b) further comprises assaying the genomic DNA of step (a) for one or more SNPs selected from the group consisting of: BICF2G630500368, BICF2P1121006, BICF2S2356299, BICF2P483191, BICF2P50610, BICF2P890246, BICF2S23324965, BICF2P544126, BICF2P526639, BICF2P1462185, BICF2P1208798, BICF2G630175389, BICF2S24415473, BICF2G630412697, BICF2P498515, BICF2P792911, BICF2G630810143, BICF2P564273, TIGRP2 P297337, BICF2G630658881, BICF2G630709791, BICF2S23147946, BICF2P181859, BICF2G630712921, BICF2G630713147, BICF2P818099, BICF2S23638642, BICF2P206910, BICF2S22959529, BICF2P1054044, BICF2S23533020, BICF2P720951, TIGRP2P31530, BICF2P247448, BICF2P1066899, BICF2G630464857, BICF2G630108404, BICF2S23148483, BICF2P866702, BICF2P1109077, BICF2P1431921, BICF2P241884, BICF2P564273, TIGRP2P46522, BICF2G630349775, BICF2S2342150, BICF2S24415473, BICF2G630359517, BICF2G63058646, BICF2P295392, BICF2G630168473, BICF2G630175389, BICF2G630810143, BICF2G630810159, BICF2G630810173, BICF2P170661, BICF2P1354767, BICF2P205255, BICF2P1358119, BICF2S23324965, BICF2S22961650, BICF2P498515, BICF2P1072682, BICF2P1090079, BCIF2P1208798, BICF2P890246, BICF2P139678, BICF2S23113199, BICF2P401973, BICF2P454456, BICF2P50610, BICF2P531097, BICF2P1290820, BICF2P65003, BICF2G630606359, BICF2S23620879, BICF2G630519882, BICF2P594418, BICF2G630422966, BICF2G630422956, BICF2G630422900, BICF2G630422895, BICF2P880005, BICF2P1121006, BICF2P888055, BICF2P582174, TIGRP2P270462, BICF2P716829, BICF2P1462185, BICF2P178583, BICF2S2328420, BICF2P420488, TIGRP2P277002, BICF2P111342, BICF2G630658881, BICF2G630658668, BICF2G630658620, BICF2G630658768, BICF2G630658756, BICF2G630658723, BICF2S2442023, BICF2S2361376, BICF2P321064, TIGRP2P293361, TIGRP2P297337, BICF2G630375268, BICF2S23730962, BICF2G630502225, BICF2G630500368, BICF2G630500363, BICF2G630500835, BICF2P544126, BICF2S24111418, BICF2G630799191, BICF2P792911, BICF2S2356299, BICF2P1332722, BICF2P1047447, BICF2P487060, BICF2P599881, BICF2P1410038, BICF2S23535135, TIGRP2P355298, BICF2S23255928, BICF2P526639, BICF2S23152419, BICF2P491441, TIGRP2P355396, BICF2P337576, BICF2P794117, BICF2P155064, BICF2P992747, BICF2S23652189, TIGRP2P362234, BICF2S23346408, 4 BICF2S23713161, BICF2S23410873, BICF2P1135545, BICF2P483191, BICF2P139173, BICF2P361907, BICF2P456086, BICF2P662502, BICF2G630412697, BICF2S2356993, BICF2P287265, BICF2S23054250, BICF2P1086740, and BICF2P708698.

7. The method of claim 6, wherein step (b) comprises assaying the genomic DNA for five or more single nucleotide polymorphisms (SNPs).

8. The method of claim 6, wherein step (b) comprises assaying the genomic DNA for ten or more single nucleotide polymorphisms (SNPs).

9. The method of claim 6, wherein step (b) comprises assaying the genomic DNA for fifteen or more single nucleotide polymorphisms (SNPs).

10. The method of claim 6, wherein step (b) comprises assaying the genomic DNA for twenty or more single nucleotide polymorphisms (SNPs).

11. The method of claim 1, further comprising
    a) isolating genomic DNA from a second dog;
    b) assaying the genomic DNA from the second dog for one or more single nucleotide polymorphisms (SNPs) wherein the one or more SNPs comprises BICF2S23652189;
    c) detecting an A allele at BICF2S23652189 in the genomic DNA of step (b); and
    d) breeding the second dog with the first dog having an "A" allele at BICF2S23652189.

12. The method of claim 11, wherein step (b) comprises assaying the genomic DNA of the second dog for five or more single nucleotide polymorphisms (SNPs).

13. The method of claim 11, wherein step (b) comprises assaying the genomic DNA of the second dog for ten or more single nucleotide polymorphisms (SNPs).

14. The method of claim 11, wherein step (b) comprises assaying the genomic DNA of the second dog for fifteen or more single nucleotide polymorphisms (SNPs).

15. The method of claim 11, wherein step (b) comprises assaying the genomic DNA of the second dog for twenty or more single nucleotide polymorphisms (SNPs).

16. The method of claim 11, wherein step (b) further comprises assaying the genomic DNA of the second dog for one or more SNPs selected from the group consisting of: BICF2G630500368, BICF2P1121006, BICF2S2356299, BICF2P483191, BICF2P50610, BICF2P890246, BICF2S23324965, BICF2P544126, BICF2P526639, BICF2P1462185, BICF2P1208798, BICF2G630175389, BICF2S24415473, BICF2G630412697, BICF2P498515, BICF2P792911, BICF2G630810143, BICF2P564273, TIGRP2P297337, BICF2G630658881, BICF2G630709791, BICF2S23147946, BICF2P181859, BICF2G630712921, BICF2G630713147, BICF2P818099, BICF2S23638642, BICF2P206910, BICF2S22959529, BICF2P1054044, BICF2S23533020, BICF2P720951, TIGRP2P31530, BICF2P247448,BICF2P1066899, BICF2G630464857, BICF2G630108404, BICF2S23148483,BICF2P866702, BICF2P1109077, BICF2P1431921, BICF2P241884, BICF2P564273, TIGRP2P46522, BICF2G630349775, BICF2S2342150, BICF2S24415473, BICF2G630359517, BICF2G63058646, BICF2P295392, BICF2G630168473, BICF2G630175389, BICF2G630810143, BICF2G630810159, BICF2G630810173, BICF2P170661, BICF2P1354767, BICF2P205255, BICF2P1358119, BICF2S23324965, BICF2S22961650, BICF2P498515, BICF2P1072682, BICF2P1090079, BICF2P1208798, BICF2P890246, BICF2P139678, BICF2S23113199, BICF2P401973, BICF2P454456, BICF2P50610, BICF2P531097, BICF2P1290820, BICF2P65003, BICF2G630606359, BICF2S23620879, BICF2G630519882, BICF2P594418, BICF2G630422966, BICF2G630422956, BICF2G630422900, BICF2G630422895, BICF2P880005, BICF2P1121006, BICF2P888055, BICF2P582174, TIGRP2P270462, BICF2P716829, BICF2P1462185, BICF2P178583, BICF2S2328420, BICF2P420488, TIGRP2P277002, BICF2P111342, BICF2G630658881, BICF2G630658668, BICF2G630658620, BICF2G630658768, BICF2G630658756, BICF2G630658723, BICF2S2442023, BICF2S2361376, BICF2P321064, TIGRP2P293361, TIGRP2P297337, BICF2G630375268, BICF2S23730962, BICF2G630502225, BICF2G630500368, BICF2G630500363, BICF2G630500835, BICF2P544126, BICF2S24111418, BICF2G630799191, BICF2P792911, BICF2S2356299, BICF2P1332722, BICF2P1047447, BICF2P487060, BICF2P599881, BICF2P1410038, BICF2S23535135, TIGRP2P355298, BICF2S23255928, BICF2P526639, BICF2S23152419, BICF2P491441, TIGRP2P355396, BICF2P337576, BICF2P794117, BICF2P155064, BICF2P992747, BICF2S23652189, TIGRP2P362234, BICF2S23346408, BICF2S23713161, BICF2S23410873, BICF2P1135545, BICF2P483191, BICF2P139173, BICF2P361907, BICF2P456086, BICF2P662502, BICF2G630412697, BICF2S2356993, BICF2P287265, BICF2S23054250, BICF2P1086740, and BICF2P708698.

17. The method of claim 16, wherein step (b) comprises assaying the genomic DNA for five or more single nucleotide polymorphisms (SNPs).

18. The method of claim 16, wherein step (b) comprises assaying the genomic DNA for ten or more single nucleotide polymorphisms (SNPs).

19. The method of claim 16, wherein step (b) comprises assaying the genomic DNA for fifteen or more single nucleotide polymorphisms (SNPs).

20. The method of claim 16, wherein step (b) comprises assaying the genomic DNA for twenty or more single nucleotide polymorphisms (SNPs).

* * * * *